United States Patent
Gillberg et al.

(10) Patent No.: US 11,642,032 B2
(45) Date of Patent: May 9, 2023

(54) MODEL-BASED THERAPY PARAMETERS FOR HEART FAILURE

(71) Applicant: Medtronic, Inc., Minneapolis, MN (US)

(72) Inventors: Jeffrey M. Gillberg, Coon Rapids, MN (US); Troy E. Jackson, Rogers, MN (US); Richard Cornelussen, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 17/120,429

(22) Filed: Dec. 14, 2020

(65) Prior Publication Data

US 2021/0196132 A1    Jul. 1, 2021

Related U.S. Application Data

(60) Provisional application No. 62/955,625, filed on Dec. 31, 2019.

(51) Int. Cl.
| | |
|---|---|
| A61B 5/00 | (2006.01) |
| A61B 5/02 | (2006.01) |
| A61B 5/361 | (2021.01) |

(52) U.S. Cl.
CPC .......... *A61B 5/02028* (2013.01); *A61B 5/361* (2021.01); *A61B 5/4836* (2013.01); *A61B 5/686* (2013.01); *A61B 5/7292* (2013.01); *A61B 5/7475* (2013.01)

(58) Field of Classification Search
CPC ........ A61N 1/3627; A61N 1/365–3688; A61N 1/3962; A61N 1/39622; A61B 5/02028; A61B 5/4842; A61B 5/7264; A61B 5/361; A61B 5/4836; A61B 5/686; A61B 5/7292; A61B 5/7475; A61B 5/7275

See application file for complete search history.

(56) References Cited

U.S. PATENT DOCUMENTS

| | | |
|---|---|---|
| 6,980,675 B2 | 12/2005 | Evron et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,321,677 B2 | 1/2008 | Evron et al. |
| 7,346,381 B2 | 3/2008 | Okerlund et al. |
| 7,454,248 B2 | 11/2008 | Burrell et al. |
| 7,499,743 B2 | 3/2009 | Vass et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,613,500 B2 | 11/2009 | Vass et al. |

(Continued)

OTHER PUBLICATIONS

International Search Report and Written Opinion from PCT Application No. PCT/US2020/065028 dated Mar. 15, 2021, 10 pages.

(Continued)

*Primary Examiner* — Scott M. Getzow
(74) *Attorney, Agent, or Firm* — Mueting Raasch Group

(57) ABSTRACT

A method includes determining that a patient has heart failure with preserved ejection fraction (HFpEF); configuring a cardiovascular (CV) model using patient characterization data; determining one or more therapy parameters using output data of the CV model; and administering HFpEF therapy based on the one or more therapy parameters.

35 Claims, 17 Drawing Sheets

(56) References Cited

U.S. PATENT DOCUMENTS

| | | |
|---|---|---|
| 7,742,629 B2 | 6/2010 | Zarkh et al. |
| 7,747,047 B2 | 6/2010 | Okerlund et al. |
| 7,778,685 B2 | 8/2010 | Evron et al. |
| 7,778,686 B2 | 8/2010 | Vass et al. |
| 7,813,785 B2 | 10/2010 | Okerlund et al. |
| 7,996,063 B2 | 8/2011 | Vass et al. |
| 8,060,185 B2 | 11/2011 | Hunter et al. |
| 8,401,616 B2 | 3/2013 | Verard et al. |
| 8,731,642 B2 | 5/2014 | Zarkh et al. |
| 8,861,830 B2 | 10/2014 | Brada et al. |
| 9,002,454 B2 | 4/2015 | Ghosh et al. |
| 9,320,446 B2 | 4/2016 | Gillberg et al. |
| 9,403,016 B2 | 8/2016 | Meyer |
| 9,737,772 B2 | 8/2017 | Jertson et al. |
| 9,877,789 B2 | 1/2018 | Ghosh |
| 9,924,884 B2 | 3/2018 | Ghosh et al. |
| 10,064,567 B2 | 9/2018 | Ghosh et al. |
| 10,251,555 B2 | 4/2019 | Ghosh et al. |
| 2005/0008210 A1 | 1/2005 | Evron et al. |
| 2006/0074285 A1 | 4/2006 | Zarkh et al. |
| 2014/0350630 A1* | 11/2014 | Rosenberg ......... A61N 1/36521 607/18 |
| 2015/0051660 A1* | 2/2015 | Meyer ............... A61N 1/36535 607/18 |
| 2015/0165198 A1 | 6/2015 | Amblard et al. |
| 2019/0290905 A1 | 9/2019 | Yang et al. |
| 2019/0290910 A1 | 9/2019 | Yang et al. |
| 2019/0290915 A1 | 9/2019 | Yang et al. |
| 2019/0298903 A1* | 10/2019 | Gillberg ............... A61B 5/6805 |
| 2020/0178850 A1* | 6/2020 | Thakur .................... A61B 7/00 |
| 2021/0074178 A1* | 3/2021 | Ilan ........................ G16H 20/60 |

OTHER PUBLICATIONS

International Preliminary Report on Patentability from PCT Application No. PCT/US2020/065028 dated Jul. 14, 2022, 7 pages.

* cited by examiner

MODEL-BASED THERAPY PARAMETERS FOR HEART FAILURE

This application claims the benefit of U.S. Provisional Patent Application. Ser. No. 62/955,625, filed on Dec. 31, 2019, which is incorporated herein by reference in its entirety.

The present technology is generally related to heart failure and, in particular, to determining therapy parameters for heart failure therapy.

Heart failure (HF) refers to a pathophysiologic disorder broadly defined by an inability of a patient's heart to pump sufficiently to cope with its venous return or to deliver sufficient output to meet the metabolic demands of the body (for example, during physical activity or in severe cases at rest). Congestive heart failure symptoms may be indicative of congestive heart failure. Congestive heart failure symptoms may include reduced cardiac output leading to easy fatigue and organ dysfunction (for example, renal dysfunction), as well as congestion either in the lungs, which may cause breathlessness, or peripherally, which may lead to swelling of the lower limbs and abdomen. In some patients, the size of the chambers of the heart may be decreased, which may occur as a result of increased muscle thickness.

A range of further sub-classifications or structure of the heart may be applied based on symptoms exhibited by the patient. Some classifications of HF by symptoms or objective assessments, for example, are provided by the New York Heart Association (classes I-IV, classes A-D)).

HF can also be defined by ejection fraction. Generally, patients exhibiting an ejection fraction of less than a threshold percentage or fraction (such as less than 0.50) are classified as having HF with reduced ejection fraction (HFrEF) while patients exhibiting an ejection fraction above the threshold or fraction (such as at least 0.50) are classified as having HF with preserved ejection fraction (HFpEF). HFpEF may be characterized by abnormal diastolic function and may be described as diastolic heart failure or diastolic dysfunction, as the deficit in function may relate to changes occurring during diastole and filling of the ventricles. The abnormal diastolic function may manifest as an increase in the stiffness of the heart's left ventricle (LV), a decrease in LV relaxation when filling with blood before the next beat, and decreased chamber volume, which may occur as a result of increased muscle thickness. Patients experiencing HFpEF may also experience other co-morbidities such as atrial fibrillation (AF) and pulmonary hypertension.

SUMMARY

The techniques of this disclosure generally relate to heart failure and, in particular, to determining therapy parameters for heart failure (HF) therapy. Heart failure patients, such as patients having heart failure with preserved ejection fraction (HFpEF), may be provided with cardiac therapy, such as pacing therapy, which may result in cardiac remodeling of the patient's heart. Cardiac remodeling may be beneficial in some cases or adverse in other cases. The present disclosure provides techniques for managing cardiac remodeling in a manner that is tailored to an individual patient or a particular group of patients, in particular, by using a cardiovascular (CV) model to facilitate determination of one or more therapy parameters. The present techniques may increase efficacy of cardiac therapy, such as HFpEF therapy using elevated heart rate (HR) pacing.

In one aspect, the present disclosure provides a therapy management method including: determining that a patient has heart failure with preserved ejection fraction (HFpEF); configuring a cardiovascular (CV) model using patient characterization data; determining one or more therapy parameters using output data of the CV model; and administering HFpEF therapy based on the one or more therapy parameters.

In another aspect, the present disclosure provides a non-transient computer-readable storage medium having computing instructions stored thereon that, when executed by processing circuitry, cause the processing circuitry to perform operations as defined in the therapy management method.

In yet another aspect, the present disclosure provides a controller including an input interface configured to receive patient characterization data; an output interface configured to provide therapy parameter data; and processing circuitry operably coupled to the input interface and the output interface The processing circuitry is configured to: receive the patient characterization data in response to determining that a patient has heart failure with preserved ejection fraction (HFpEF); configure a cardiovascular (CV) model using the patient characterization data; determine one or more therapy parameters using output data of the CV model; and provide therapy parameter data including the one or more therapy parameters to the output interface.

In still another aspect, the present disclosure provides a system including: one or more patient characterization devices to provide patient characterization data; an implantable medical device (IMD) configured to provide heart failure with preserved ejection fraction (HFpEF) pacing therapy; and processing circuitry operably coupled to the one or more patient characterization devices and the implantable medical device. The processing circuitry is configured to: receive the patient characterization data in response to determining that a patient has HFpEF; configure a cardiovascular (CV) model using the patient characterization data; determine one or more therapy parameters using output data of the CV model; and configure the IMD to provide HFpEF pacing therapy based on the one or more therapy parameters.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
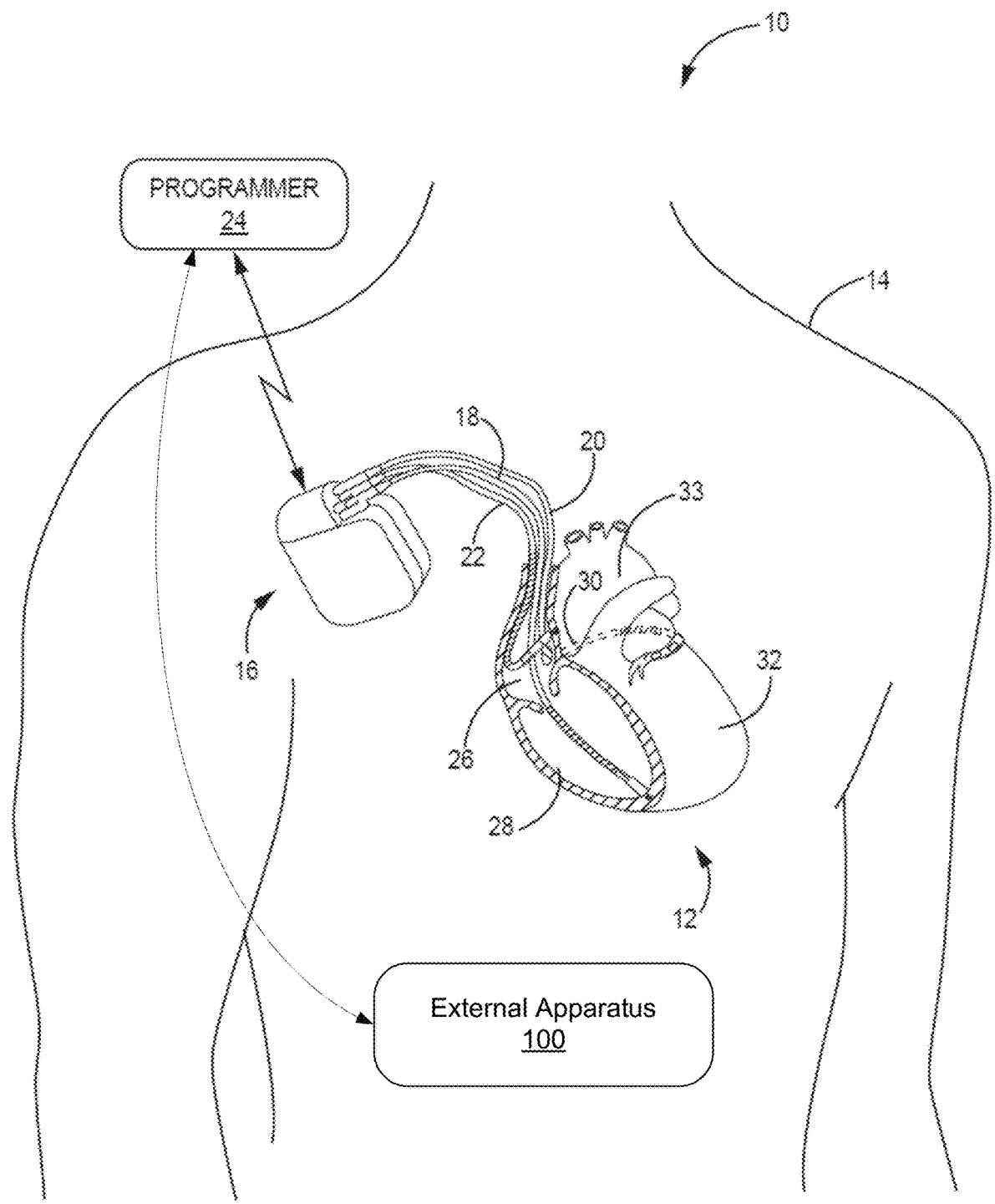
FIG. 1 is a conceptual diagram that illustrates one example of a cardiac therapy delivery system that may be used to deliver a pacing therapy according to the present disclosure.

The techniques of this disclosure generally relate to heart failure and, in particular, to determining therapy parameters for heart failure (HF) therapy. Heart failure patients, such as patients having heart failure with preserved ejection fraction (HFpEF), may be provided with cardiac therapy, such as pacing therapy, which may result in cardiac remodeling of the patient's heart. Cardiac remodeling may be beneficial in some cases or adverse in other cases. The present disclosure provides techniques for managing cardiac remodeling in a manner that is tailored to an individual patient or a particular group of patients, in particular, by using a cardiovascular (CV) model to facilitate determination of one or more therapy parameters. The present techniques may increase efficacy of cardiac therapy, such as HFpEF therapy using elevated heart rate (HR) pacing.

HF may be treated using cardiac pacing therapy. Cardiac therapy may be, or include, HFpEF therapy to treat patients having HFpEF. In some embodiments, HFpEF therapy may include periodic high, or elevated, heart rate (HR) pacing. Elevated heart rate pacing for HFpEF therapy may remodel the patient's heart. HFpEF therapy may also be described as cardiac remodeling pacing therapy. Any suitable technique for cardiac remodeling pacing therapy may be used known to one skilled in the art having the benefit of the present disclosure. Non-limiting examples of cardiac remodeling pacing therapy are described in U.S. Pat. No. 9,403,016 (Meyer), issued Aug. 2, 2016, and U.S. Pat. No. 9,737,772 (Meyer), issued Aug. 22, 2017, which are incorporated herein by reference in their entireties.

In general, HFpEF therapy according to the present disclosure is configured to manage the delivery of elevated HR pacing, for example, by using a CV model to facilitate predicting the remodeling response of the patient. For example, the HFpEF therapy may stop elevated HR pacing based on output data from the CV model to prevent increasing the volume of the patient's heart beyond a certain threshold, which may be described as a dilatation threshold. In general, the HFpEF therapy may be managed to balance the diastolic and systolic functions. Such management may prevent excessive dilatation and HFrEF.

Cardiac therapy may be provided by implantable medical devices (IMDs), which may be programmable based on one or more therapy parameters. Therapy provided by IMDs for cardiac disease may be delivered effectively by tailoring therapy to individual patients. Patient characterization data may be collected for feedback, for example, from an electrode apparatus (for example, an electrocardiogram (ECG)) or echocardiogram. Patient characterization data may be used to predict chronic remodeling in a therapy modeling system. In particular, prediction of chronic remodeling using the therapy modeling system may be based on configuring a cardiovascular (CV) model with patient characterization data. The CV model may also be described as, or include, a physiologic model representative of at least part of the patient's cardiovascular system. The therapy modeling system may determine and recommend appropriate therapy parameters for patients based on output data of the CV model. In one example, the CV model may be used to determine that pacing therapy is not predicted to lead to remodeling (dilatation) and is predicted to provide hemodynamic benefits, in which case, pacing therapy may continue.

Programmable IMD therapy for cardiac disease may be delivered more effectively by tailoring therapy to an individual patient or particular group of patients. The therapy parameters may be determined to be optimal therapy parameters to provide therapeutic effect to the individual patient or particular group of patients. In some embodiments, the patient characterization data may be used to determine a patient classification, such as a patient cohort or patient micro-cohort, which may be used to configure the CV model to provide targeted output data to more accurately indicate a predicted patient response to cardiac therapy. Therapy parameters determined by the therapy modeling system based on the targeted output data may be optimal for the patient in the cohort or micro-cohort.

In some embodiments, the therapy modeling system may provide generic patient descriptors to characterize a patient cohort. For example, a generic patient descriptor may classify the patient as having HFpEF with concentric hypertrophy or as having HFpEF without concentric hypertrophy. Other descriptions of phenotypes of cardiac disease may also be provided based on patient history data, which may be based on prior testing recorded in an electronic medical record (EMR), or may be driven by particular parameters measured from the patient during, or in advance of, a programming session with or without patient history data.

In some embodiments, recommended therapy parameters from the therapy modeling system may be used for initial IMD or other medical device programming and may also be used during one or more patient follow-ups. In some embodiments, the initial CV model may be configured based on patient baseline data alone. The CV model may be updated in a follow-up CV model, which may be configured based on patient response data at a "point in time" after administering cardiac therapy.

As used herein, the term "patient characterization data" refers to data based on measurements or other stored data about a patient or about a particular group with which the patient is associated. In some embodiments, patient characterization data may be based on measured data, such as clinical measurement data (for example, "point in time" measurements in a clinical setting), ambulatory measurement data (for example, recorded by an IMD or other ambulatory medical device), or both.

Non-limiting examples of clinical measurement data include clinician input, electrode apparatus data, echocardiogram data, imaging data, patient history data, hemodynamic measurement data, or IMD data.

Non-limiting examples of ambulatory measurement data include daily or night heart rate, heart rate variability, patient activity levels, contractility measures, or cardiac auscultation or heart sounds.

As used herein, the term "patient response data" refers to a type of patient characterization data based on measurements after administering cardiac therapy. Patient response data may be measured in the same or similar manner to other patient characterization data. Patient response data may be based on measured data, such as clinical measurement data, ambulatory measurement data, or both.

In some embodiments, for HFpEF therapy, various therapy parameters, such as programmable device parameters, may be recommended by the therapy modeling system. The therapy modeling system may also provide recommendation of therapy "aggressiveness" based on the patient's prior response to therapy. The patient's prior response may be determined from ambulatory diagnostic measurements or "point-in-time" measurements, such as serial echocardiographic data or other means of measuring progression of remodeling. For example, the high rate pacing HFpEF therapy may result in cardiac dilation. The therapy modeling system may provide recommendations to stop therapy or reduce aggressiveness based on generic patient classifications or specific patient measurements of cardiac dilation or structure compared to predetermined thresholds. The therapy modeling system may also increase aggressiveness based on lack of evidence of cardiac structure changes.

In some embodiments, the therapy modeling system may incorporate a "cloud-based" system and be accessible over the internet. The therapy modeling system may receive, or request, patient characterization data and provide recommendations to the clinician, for example, on a user interface device. In other embodiments, the therapy modeling system may be based on a device programmer, or on a stand-alone computer, that provides information during programmer sessions. In some embodiments, automated approaches may combine the cloud-based system with a programmer, or other device, to create an integrated system for programming recommendations. In some embodiments, a fully automated approach to the therapy modeling system may be fully implemented in an IMD and programmer system, which may not need to access the cloud.

Although the present disclosure makes reference to HF and particularly HFpEF therapy, the techniques of this disclosure may also be adapted for other types of implantable therapy devices, such as cardiac resynchronization therapy (CRT) devices or left ventricular assist devices (LVADs). In general, a CV model may be used to manage various therapies by simulating the patient's response to such therapies.

All scientific and technical terms used herein have meanings commonly used in the art unless otherwise specified. The definitions provided herein are to facilitate understanding of certain terms used frequently herein and are not meant to limit the scope of the present disclosure.

As used herein, the terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out certain functionality.

As used herein, the term "configured to" may be used interchangeably with the terms "adapted to" or "structured to" unless the content of this disclosure clearly dictates otherwise.

The term "or" is generally employed in its inclusive sense, for example, to mean "and/or" unless the context clearly dictates otherwise. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 is a conceptual diagram that illustrates one example of a cardiac therapy delivery system 10 that may be used to deliver a pacing therapy. In general, the cardiac therapy delivery system 10 may include any suitable components for delivering cardiac therapy based on one or more model-based therapy parameters.

In some embodiments, the therapy delivery system 10 may include one or more devices to provide cardiac therapy to a patient 14 using model-based therapy parameters from a therapy. In some embodiments, the system 10 may include one or more IMDs to carry out cardiac therapy. One or more IMDs may be configured to detect electrical activity in one or more chambers of the patient's heart 12. One or more IMDs may be used to detect the ventricular electrical activity, atrial electrical activity, or even mechanical activity of one or more chambers of the heart 12. In particular, one or more electrodes may be used to sense, or detect, electrical activity, and one or more motion sensors may be used to sense, or detect, mechanical activity.

In the illustrated embodiment, the therapy delivery system 10 includes an implantable medical device 16 (IMD), which may be coupled to leads 18, 20, 22 and a programmer 24. The IMD 16 may be, for example, an implantable pacemaker, cardioverter, or defibrillator, that provides electrical signals to the heart 12 of a patient 14 via electrodes coupled to one or more of the leads 18, 20, 22. Patient 14 may, but not necessarily, be a human.

The leads 18, 20, 22 extend into the heart 12 of the patient 14 to sense electrical activity of the heart 12 or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12. In one example, the atrial lead 22 can be positioned near the AV nodal/septal area for delivery of His bundle pacing and at least one the ventricular lead 18 is positioned in the right ventricle or the ventricular lead 20 is positioned in the left ventricle, as described below. In some embodiments (not shown), one or more leads may extend into the left atrium 33 (LA) of the patient's heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (for example, pacing pulses) to the heart 12 based on the electrical signals sensed within the heart 12. The IMD 16 may be operable to adjust one or more parameters associated with the pacing therapy such as, for example, pulse duration, voltage amplitude, burst length, etc. Further, the IMD 16 may be operable to use various electrode configurations to deliver pacing therapy, which may be unipolar or bipolar. The IMD 16 may also provide defibrillation therapy or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, for example, pulses with increasing energy levels, until a fibrillation of heart 12 is stopped.

The therapy delivery system 10 may include one or more leadless IMDs (not shown). Any suitable leadless IMD may be included, such as leaded IMDs, leadless IMDs, or intracardiac IMDs.

As used herein, a "leadless" device refers to a device being free of a lead extending out of the heart 12. In other words, a leadless device may have a lead that does not extend from outside of the heart 12 to into the inside of the heart. Some leadless devices may be introduced through a vein, but once implanted, the leadless device is free of, or may not include, any transvenous lead and may be configured to provide cardiac therapy without using any transvenous lead. In one example, a leadless device implanted in the left ventricle (LV), in particular, does not use a lead to operably connect to an electrode in the LV when a housing of the device is positioned in the LV. One or more leaded or leadless electrodes may be coupled to the housing of an IMD. An IMD having only leadless electrodes may be described as a leadless IMD. In some embodiments, a leadless IMD may include a leadlet, which may extend from a chamber of the heart into to another location in the heart 12 or in the vasculature of the patient 14.

As used herein, a "leadless" electrode refers to an electrode operably coupled to a device being free of a lead, or without using a lead, extending between the electrode and the housing of the device.

As used herein, an "intracardiac" device refers to a device configured to be implanted entirely within the heart 12. An intracardiac IMD may include a leadlet, which does not extend out of the heart 12.

Another type of IMD that may be used in the therapy delivery system 10 is a ventricle-from-atrium (VfA) IMD. Non-limiting examples of VfA IMDs are described in U.S. Publication No. 2019/0290905 (Yang et al.), filed Mar. 22, 2019; U.S. Publication No. 2019/0290910 (Yang et al.), filed Mar. 22, 2019; and U.S. Publication No. 2019/0290915 (Yang et al.), filed Mar. 22, 2019, which are incorporated herein by reference in their entireties.

One or more devices of the therapy delivery system 10 may include a motion sensor 38. The motion sensor may be configured to sense mechanical activity of the patient 14 or of the patient's heart 12. In some cases, the motion sensor 38 may be configured to sense at least mechanical activity of one or both atria (left, right, or both) of the patient's heart 12. Non-limiting examples of a motion sensor include an inertial measurement unit (IMU), such as an accelerometer, gyroscope, or magneto-sensors.

In some embodiments, mechanical activity detected by the motion sensor 38 may correspond to various heart sounds. In general, heart sounds are associated with mechanical vibrations of a patient's heart and the flow of blood through the heart valves and, thus, may be highly correlated with pressure gradients across heart valves and blood pressure. Heart sounds may be not only due to vibrations of and pressure within the heart, but may also be due to the entire cardiohemic system, such as blood, great arteries, etc. Heart sounds may recur with each cardiac cycle and are separated and classified according to the activity associated with the vibration.

The first heart sound is referred to as "S1," and can be thought of as the vibration sound made by the heart during closure of the atrioventricular, or AV, valves, i.e., the mitral valve and tricuspid valve. The S1 sound can sometimes be broken down into the M1 sound component, from the closing of the mitral valve, and the T1 sound component, from the closing of the tricuspid valve. The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 sound component is from the closing of the pulmonary valve and the A2 sound component is from the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricles from the atria. S4 is caused by blood rapidly filling into the ventricles from the atria due to atrial contraction.

Figure 4:
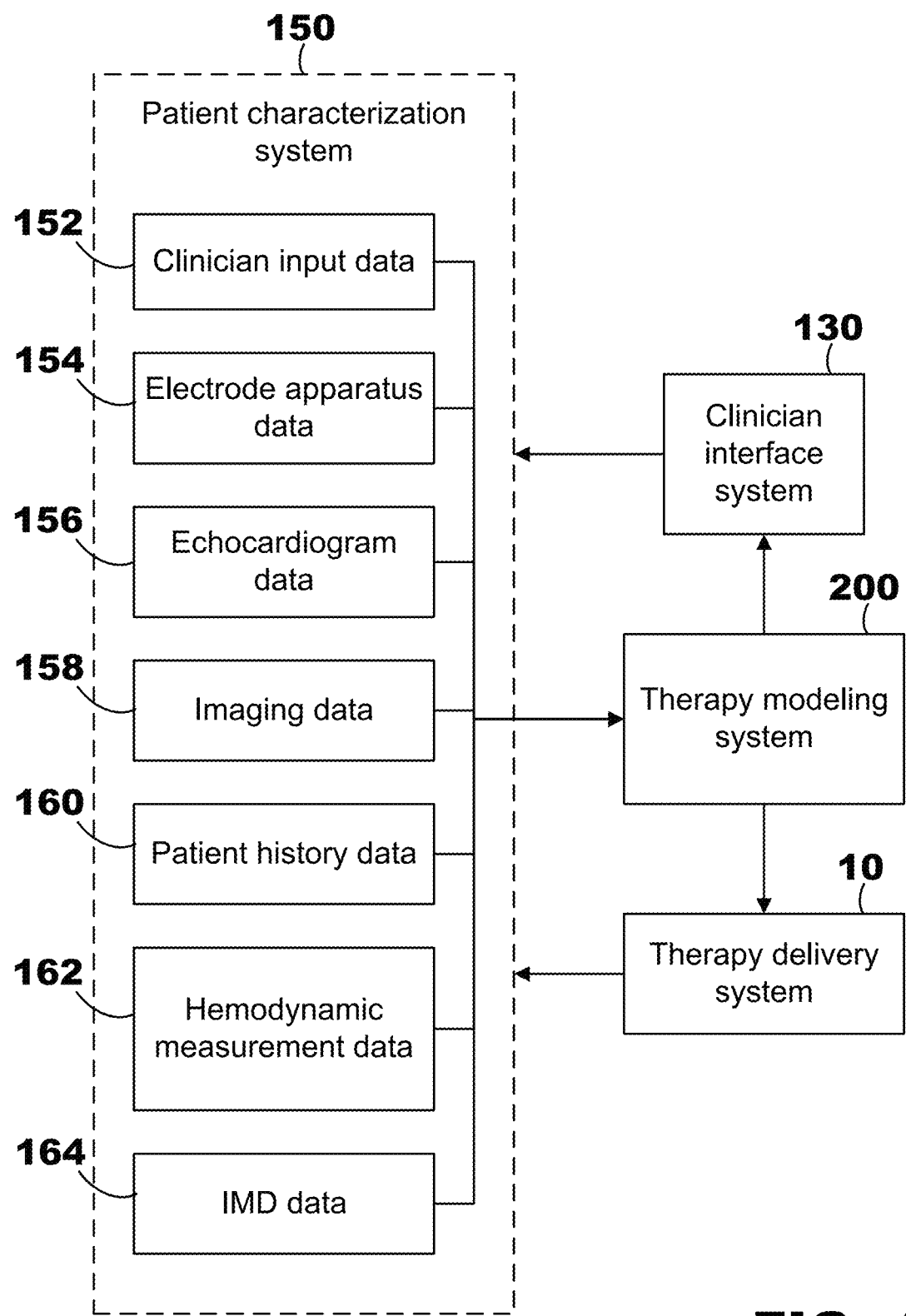
FIG. 4 is a conceptual diagram that illustrates one example of a therapy modeling system and a patient characterization system usable with the cardiac therapy delivery system of FIG. 1.

The therapy delivery system 10 may be operably coupled to a therapy modeling system 200 (FIG. 4). The therapy delivery system 10 may receive one or more therapy parameters to deliver cardiac therapy to the patient 14. The therapy delivery system 10 may deliver and manage cardiac therapy to a patient experiencing or having HFpEF to appropriately manage HFpEF therapy based on the one or more therapy parameters from the therapy modeling system 200.

In some embodiments, a programmer 24, which may be a handheld computing device, a computer workstation, or other user interface device for a user, such as a physician, technician, another clinician, or patient, to communicate with the IMD 16 (for example, to program the IMD 16). For example, the user may interact with the programmer 24 to retrieve information concerning one or more detected or indicated faults associated within the IMD 16 or the pacing therapy delivered therewith. The IMD 16 and the programmer 24 may communicate via wireless communication using any suitable techniques. Examples of communication techniques may include, for example, low frequency or radiofrequency (RF) telemetry, but other techniques are also contemplated.

The programmer 24 may be operably coupled to a network or the internet to facilitate communication between the IMD 16 and other devices. The programmer 24 may be described as an access point or communication link. The programmer 24 may also be described as having a transceiver. In some embodiments, the programmer 24 may be used to operably couple the IMD 16 to a therapy modeling system 200 (FIG. 4).

The therapy delivery system 10 may include an external apparatus 100 positionable outside of the body of the patient 14. The external apparatus 100 may be positioned proximate to the body. In some embodiments, the external apparatus 100 may include one or more components to facilitate evaluation of various implantation locations (such as spatial location, implant depth, etc.) or pacing settings (such as pulse width, pulse timing, pulse amplitude, etc.). For example, implantation location of or pacing delivered by one or more electrodes of the IMD 16. The external apparatus 100 may include one or more of an electrode apparatus, a display apparatus, and a computing apparatus as will be described further herein with respect to FIGS. 6-8. In one example, the electrode apparatus of the external apparatus 100 may include a plurality of electrodes configured to provide electrical heterogeneity information (EHI) that may be used to evaluate the various implantation locations or paced settings. The programmer 24 may also be operably coupled to the external apparatus 100. In some embodiments, the programmer 24 may be used to operably couple the external apparatus 100 to a therapy modeling system 200 (FIG. 4).

Figure 2:
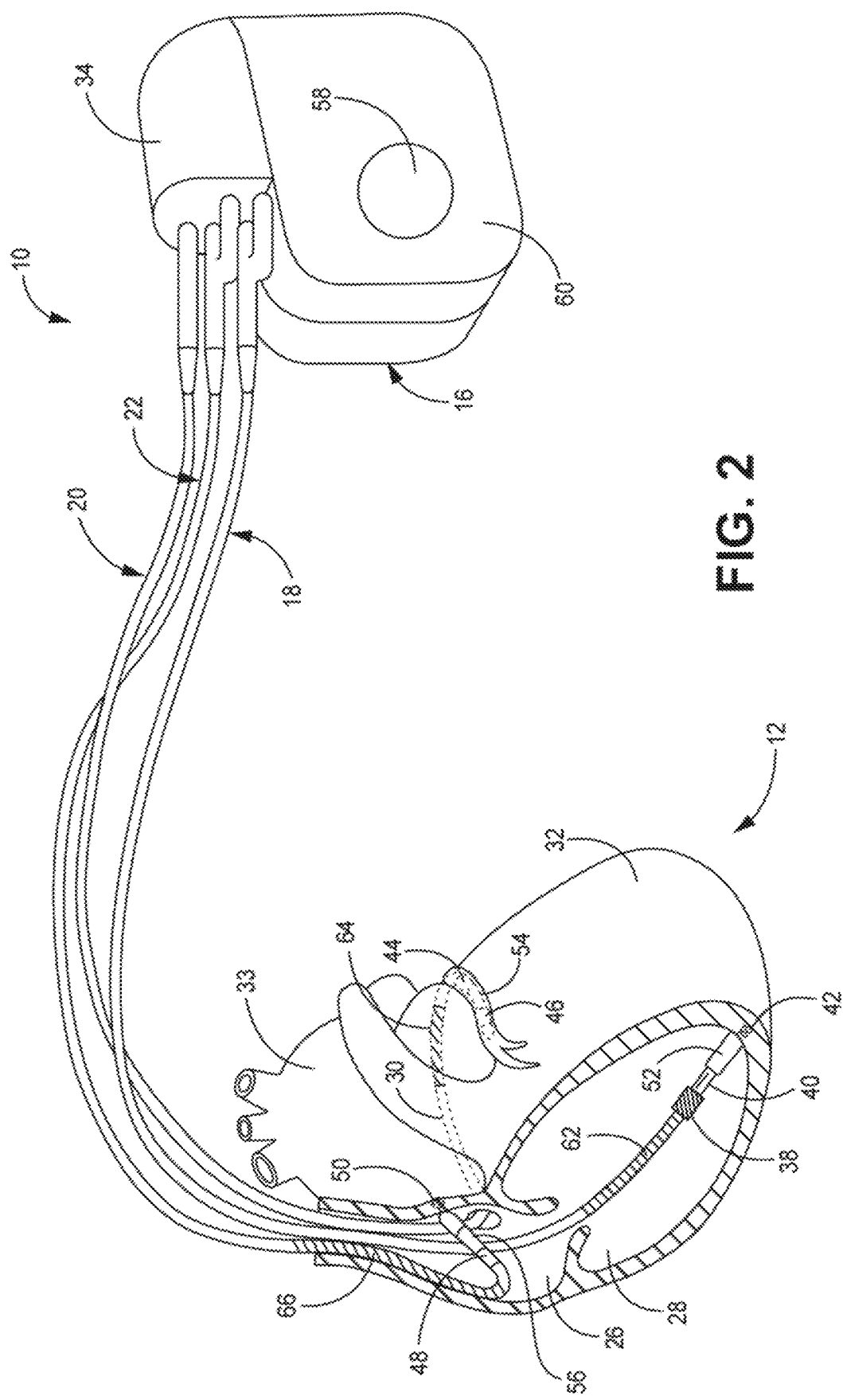
FIG. 2 is a conceptual diagram that illustrates the cardiac therapy delivery system of FIG. 1.

FIG. 2 is a schematic diagram that illustrates the exemplary cardiac therapy delivery system of FIG. 1 in more detail. The leads 18, 20, 22 may be electrically coupled to a therapy delivery module (for example, for delivery of pacing therapy), a sensing module (for example, one or more electrodes to sense or monitor electrical activity of the heart 12 for use in determining effectiveness of pacing therapy), or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (for example, concentric coiled conductors, straight conductors, etc.) separated from one another by insulation (for example, tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (for example, coiled or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (for example, morphological waveforms within electrograms (EGM)) attendant to the depolarization and repolarization of the heart 12. The sensed electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (for example, hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, for example, a sensing vector that may be used to evaluate or analysis the effectiveness of pacing therapy. An example of a configuration sensing and pacing may be seen with respect to U.S. Pat. No. 9,002,454 filed Dec. 23, 2011, which is incorporated by reference in its entirety, which may be modified by using an $LV_{tip}$-$RV_{coil}$ (such as electrode 46 and electrode 62, respectively) for the pacing vector and the sensing vector. The $LV_{tip}$ to $RV_{coil}$ vector may be better for performing impedance measurements. This impedance may be inversely correlated to LV chamber size and may drop as the LV chamber dilates with remodeling pacing. It is generally understood by those skilled in the art having the benefit of this disclosure that other electrodes can also be selected as pacing and sensing vectors.

As described in further detail with reference to FIG. 3, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, or other materials known to be usable in implantable defibrillation electrodes. Since electrodes 62, 64, 66 are not generally configured to deliver pacing therapy, any of electrodes 62, 64, 66 may be used to sense electrical activity during pacing therapy (for example, for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (for example, in combination with the housing electrode 58 forming a RV elongated, coil, or defibrillation electrode-to-housing electrode vector).

One example configuration of the therapy delivery system 10 illustrated in FIGS. 1-2 is merely one example. In one example, the atrial lead 22 is positioned near the AV nodal/septal area for delivery of His bundle pacing (and may sense or pace the RA or LA) and either the ventricle lead 18 is positioned in the right ventricle or the ventricle lead 20 positioned in the left ventricle, or both ventricle leads 18 and 20 may be included, as described below. In addition, the electrode 50 of lead 22 may take the form of a helical tip electrode to enable the lead to be fixedly engaged near the AV nodal/septal area for delivery of His bundle pacing, described below.

Figure 3:
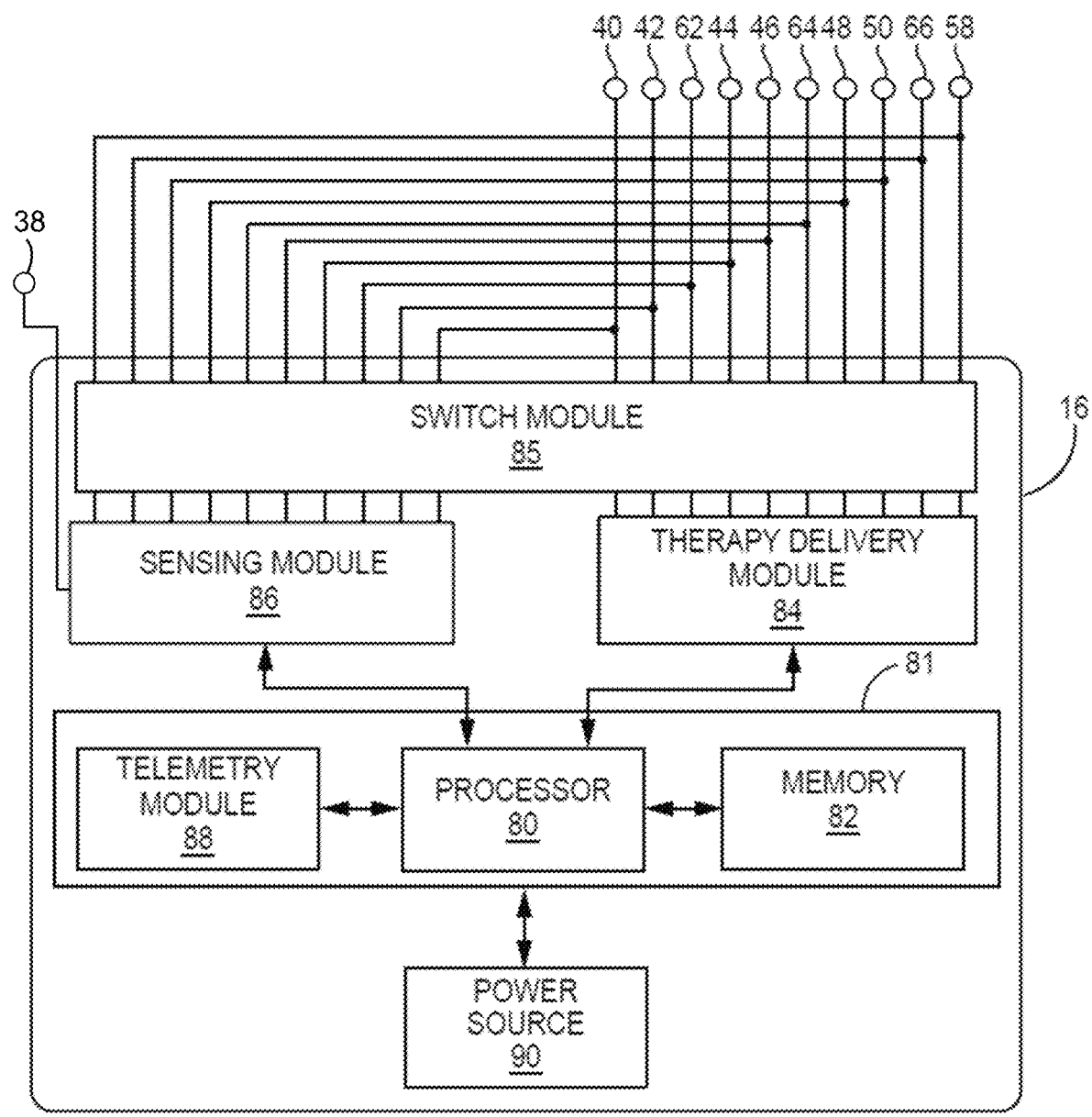
FIG. 3 is a conceptual diagram that illustrates one example of a configuration the cardiac therapy delivery system of FIG. 1.

FIG. 3 is a conceptual diagram that illustrates one example of a configuration of the IMD 16. As illustrated in FIG. 3, the IMD 16 may include processing circuitry, which may include a control module 81 (or controller), a therapy delivery module 84 (or therapy delivery circuitry), which may include a stimulation generator, a sensing module 86 (or sensing circuitry), and a power source 90.

The control module 81 may include a processor 80, memory 82, and a telemetry module 88. The IMD 16 may also include a motion sensor 38 (FIG. 2) operably coupled to the processor 80, for example, through the sensing module 86.

The memory 82 may include computer-readable instructions that, when executed, for example, by the processor 80, cause the IMD 16 or the control module 81 to perform various functions attributed to the IMD 16 or the control module 81 described herein. Further, the memory 82 may include any volatile, non-volatile, magnetic, optical, or electrical media, such as a random-access memory (RAM), read-only memory (ROM), non-volatile RAM (NVRAM), electrically erasable programmable ROM (EEPROM), flash memory, or any other digital media. Memory 82 includes computer instructions related to capture management, including the method of capture management according to the present disclosure, described in detail below. Furthermore, memory 82 includes computer instructions for one or more pacing regimen(s) (for example, one or more pacing algorithm(s)).

In general, one or more pacing algorithms of the present disclosure may be dynamically employed to up-titrate or down-titrate cardiac rhythms and heart rates. In one example, one or more pacing algorithms pace the heart at an elevated heart rate for a specified duration followed by pacing the heart at a second heart rate level for another pre-specified duration of time. In another example, one or more pacing algorithms pace the heart at a first elevated rate and a first duration. In yet another example, one or more pacing algorithms pace the heart at a first elevated pacing rate (for example, up to 30 heart beats per minute above resting heart rate for up to 10 minutes or up to 20 minutes. Thereafter, the pacing rate is elevated to a second elevated pacing rate (for example, up to 20 HBPM above the first elevated heart rate for up to 10 or 20 minutes). Thereafter a third pacing rate is delivered to allow the heart to beat more slowly than the second elevated pacing rate. A fourth pacing rate, lower than the third pacing rate, is delivered to the heart through a pacemaker. Thereafter, the heart rate is allowed to gradually return to a resting heart rate level (with or without pacing). Multiple other pacing regimens are disclosed herein that may be employed by a pacemaker in order to remodel the heart.

The processor 80 (also referred to as processor circuit) of the control module 81 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (for example, electrical stimulation therapy such as pacing) to the heart 12 according to a selected one or more therapy programs, which may be stored in the memory 82. More, specifically, the control module 81 (for example, the processor 80) may control the therapy delivery module 84 to deliver electrical stimulus such as, for example, pacing pulses with the amplitudes, pulse widths, frequency, or electrode polarities specified by the selected one or more therapy programs (for example, pacing therapy programs, pacing recovery programs, capture management programs, etc.). As shown, the therapy delivery module 84 is electrically coupled to electrodes 40, 42, 44, 46, 48, 50, 58, 62, 64, 66, for example, via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (for example, pacing pulses) via ring electrodes 40, 44, 48 coupled to leads 18, 20, and 22, respectively, or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, or other substantially continuous time signals.

The IMD 16 may further include a switch module 85 and the control module 81 (for example, the processor 80) may use the switch module 85 to select, for example, via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 or the therapy delivery module 84 to one or more selected electrodes. More specifically, the therapy delivery module 84 may include a plurality of pacing output circuits. Each pacing output circuit of the plurality of pacing output circuits may be selectively coupled, for example, using the switch module 85, to one or more of the electrodes 40, 42, 44, 46, 48, 50, 58, 62, 64, 66 (for example, a pair of electrodes for delivery of therapy to a pacing vector). In other words, each electrode can be selectively coupled to one of the pacing output circuits of the therapy delivery module using the switching module 85.

The sensing module 86 is coupled (for example, electrically coupled) to sensing apparatus, which may include, among additional sensing apparatus, the electrodes 40, 42, 44, 46, 48, 50, 58, 62, 64, 66 to monitor electrical activity of the heart 12, for example, electrocardiogram (ECG)/electrogram (EGM) signals, etc. The ECG/EGM signals may be used to analyze a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (the segment that connects the QRS complex and the T-wave), T-wave changes, QT intervals, electrical vectors, etc.

The switch module 85 may be also be used with the sensing module 86 to select which of the available electrodes are used to, for example, sense electrical activity of the patient's heart (for example, one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, for example, by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (for example, using the processor 80) may employ digital signal analysis techniques to characterize the digitized signals stored in memory 82 to analyze or classify one or more morphological waveforms of the EGM signals to determine pacing therapy effectiveness. For example, the processor 80 may be configured to determine, or obtain, one or more features of one or more sensed morphological waveforms within one or more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (for example, no pacing), "A" may indicate an atrium, and "R" may indicate rate responsive. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, or the pulse widths of the pacing pulses. As another example, the pacer timing and control module may define a blanking period and provide signals from sensing module 86 to blank one or more channels, for example, amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (for example, including a stimulation generator) may include one or more pacing output circuits that are coupled, for example, selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, for example, the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal or external. The processor 80 may provide the data to be uplinked to the programmer 24 and the control signals for the telemetry circuit within the telemetry module 88, for example, via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (for example, does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, for example, on a daily or weekly basis.

One or more components of the IMD 16 may define an implantable pulse generator (IPG) circuit. The IPG generates pacing pulses to cardiac tissue. Typically, pacing pulses can be timed to a target heart rate for each patient. To adjust a patient's heart rate, the interval between pacing pulses is adjusted by the pacemaker. For example, to increase a patient's heart rate, the interval between pulses generated from the pacemaker is decreased. In contrast, to decrease a patient's heart rate, the interval between pulses is increased. In one or more embodiments, an exercise regimen may be configured to include exercise intervals (for example, a higher target heart rate that is higher than a patient's resting heart rate level) interleaved with recovery intervals (for example, a lower target heart rate that are lower than an immediately preceding exercise interval). One target heart rate zone for exercising the heart may be 50% to 85% of a patient's maximum heart rate. In one or more embodiments, the target heart rate zone can be set to 75% to 95% of the patient's maximum heart rate zone. In one or more other embodiments, the target heart rate zone can be set up to 105% of the patient's maximum heart rate zone for a short period of time (for example, up to 20, 30, or more minutes).

The exercise regimens, including a set of increased rate intervals interleaved with recovery rate intervals (also referred to as reduced rate intervals), can be implemented by using a base rate that is adjusted by modifying the pacing pulses for each interval. For example, if the resting heart rate is the base rate from which the intervals are measured, then the first increased rate can be determined by taking the average resting heart rate for that patient (for example, 60 heart beats per minute (HBPM)) and adding a pre-specified number of HBPM (for example, 20 HBPM) for that particular interval to obtain 80 HBPM (or 60 HBPM+20 HBPM) over a first time period (for example, 10 minutes). Since the target heart rate level is now 80 HBPM, the interval between pulses generated from the pacemaker is decreased.

The pacemaker can be configured to use the maximum heart rate level as a base rate and a target rate would be adjusted down from the maximum heart rate to a target heart rate zone (for example, 50% to 85% of the maximum heart rate zone). The patient's maximum heart rate can be determined by using the patient's tracked daily activities or using known equations (such as 220 HBPM minus the patient's age). Maximum heart rate can depend on a variety of factors including the patient's age, physical activity, and heart condition.

The pacemaker may be configured to automatically track a person's heart rate for a certain period of time (for example, one day) and customize the pacing pulse intervals in response to the patient's activity. The activity sensor senses the person's activities throughout the day and the processor adjusts the pacing rate of the pacemaker to the patient's activities.

Various other types of sensors may also be used, such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

FIG. 4 is a conceptual diagram that illustrates one example of a therapy modeling system 200 and a patient characterization system 150 operably coupled to one another. The therapy modeling system 200 may be configured to receive patient characterization data from the patient characterization system 150.

The patient characterization system 150 may include one or more devices that are configured to provide various types of patient characterization data. Although the patient characterization system 150 is shown separately from the therapy modeling system 200 and the therapy delivery system 10, some devices of the patient characterization system may also be included in the therapy modeling system or therapy delivery system, or vice versa, such as the IMD 16 (FIG. 1).

In some embodiments, the patient characterization system 150 may be configured to provide clinician input data 152. The patient characterization system 150 may include, or be operably coupled to, a clinician interface system 130. The clinician interface system 130 may include any suitable user interface device to provide information to or to receive input from a clinician. Non-limiting examples of user interface devices include a keyboard, a mouse, a display, a touchscreen, or a button. The clinician interface system 130 may provide clinician input data 152 to the patient characterization system 150, which may then be provided to the therapy modeling system 200 for use in managing cardiac therapy. Non-limiting examples of clinician input data 152 may include a patient classification, or diagnosis, of HFpEF, response to medication, or concomitant device information (such as therapies provided by other devices).

In some embodiments, the patient characterization system 150 may be configured to provide electrode apparatus data 154. The patient characterization system 150 may include, or be operably coupled to, an electrode apparatus, such as electrode apparatus 510 (FIGS. 6-8), which may be part of the external apparatus 100 (FIG. 1). The electrode apparatus data 154 may include data from an ECG, ECG belt, or ECG vest. Non-limiting examples of electrode apparatus data 154 include one or more cardiac dyssynchrony measures, such as standard deviations of LV activation times (SDATs) or other measures described with respect to FIGS. 6-8.

In some embodiments, the patient characterization system 150 may be configured to provide echocardiogram data 156. The patient characterization system 150 may include, or be operably coupled to, an ultrasound system (not shown) configured to provide an echocardiogram, which may be part of the external apparatus 100 (FIG. 1). Any suitable ultrasound system known to one skilled in the art having the benefit of this disclosure may be used. The echocardiogram data 156 may include data from the ultrasound system, such as echocardiograms or other ultrasound data. Non-limiting examples of echocardiogram data 156 include cardiovascular or cardiac measures, which may be related to structure, dimension, volume, size, or mass. In some embodiments, echocardiogram data 156 may be used to indicate one or more chamber wall thicknesses, one or more volumes, and various functions (such as ejection fraction) of patient's heart during the cardiac cycle. In some embodiments, echocardiogram data 156 may be used to indicate conditions such as concentric hypertrophy or concentric remodeling.

In some embodiments, the patient characterization system 150 may be configured to provide imaging data 158. Imaging data 158 may be used to characterize the patient's heart, vasculature, or other portions of the patient's body. The patient characterization system 150 may include, or be operably coupled to, an imaging system (not shown), which may be part of the external apparatus 100 (FIG. 1). Any suitable imaging system known to one skilled in the art having the benefit of this disclosure may be used, such as a magnetic resonance imaging (MRI) scan system or CT scan system. The imaging data 158 may include data from the imaging system, such as Mill images or X-ray images. Non-limiting examples of imaging data 158 include chamber dimensions, chamber function, fibrosis, and metabolic state. In some embodiments, imaging data 158 may be used to indicate various conditions, such as systemic diseases (such as microvascular dysfunction) and comorbidities (such as diabetes). In some embodiments, imaging data may be defined as also including echocardiogram data.

In some embodiments, the patient characterization system 150 may be configured to provide patient history data 160. The patient characterization system 150 may include, or be operably coupled to, a data storage system, which may be part of the external apparatus 100 (FIG. 1). Any suitable data storage system known to one skilled in the art having the benefit of this disclosure may be used, such as a computer server hosting a patient database. The patient history data 160 may include data from previous measurements or inputs. Non-limiting examples of patient history data 160 include a previous classification of concentric hypertrophy or concentric remodeling, a previous classification of HFpEF, or any other suitable information about the patient that may be useful in managing therapy.

In some embodiments, the patient characterization system 150 may be configured to provide hemodynamic measurement data 162. The patient characterization system 150 may include, or be operably coupled to, a hemodynamic measurement system (not shown), which may be part of clinically invasive medical device. Any suitable hemodynamic measurement system known to one skilled in the art having the benefit of this disclosure may be used, which may include a right heart or left heart catheterization to measure pressures and volumes in the patient's heart or vasculature. The hemodynamic measurement data 162 may include data from previous measurements or inputs. Non-limiting examples of hemodynamic measurement data 162 include a left ventricular end diastolic pressure (LVEDP), central venous pressure, or left ventricular pressure or volumes (such as LVEDD). In some embodiments, hemodynamic measurement data 162 may be used to indicate a response to therapy or a baseline.

In some embodiments, the patient characterization system 150 may be configured to provide IMD data 164. The IMD data 164 may be provided, for example, by an IMD, such as IMD 16 (FIG. 1). Non-limiting examples of IMD data 164 include daily or night heart rate, heart rate variability, patient activity levels, contractility measures, and cardiac auscultation (or heart sounds).

The patient characterization data from the patient characterization system 150 may be used by the therapy modeling system 200 in any suitable manner. In some embodiments, in response to determining that the patient has HF, or specifically HFpEF, the patient characterization data may be used to configure a CV model stored and executed by the therapy modeling system 200. The therapy modeling system 200 may determine one or more therapy parameters based on output data from the CV model. HF therapy, such as HFpEF therapy, may be administered based on the one or more therapy parameters. In some embodiments, in response to determining that the patient does not have HFpEF, the patient may be tested or treated for a different condition, such as electrical or mechanical dyssynchrony. In some embodiments, after administering HF therapy, the therapy modeling system 200 may update the CV model based on patient response data. In some embodiments, the patient response data may be provided as patient characterization data from the therapy delivery system 10 or the clinician interface system 130, through the patient characterization system 150. The therapy modeling system 200 may update HF therapy based on the updated CV model. Further functionality of the therapy modeling system 200 is described herein.

Figure 5:
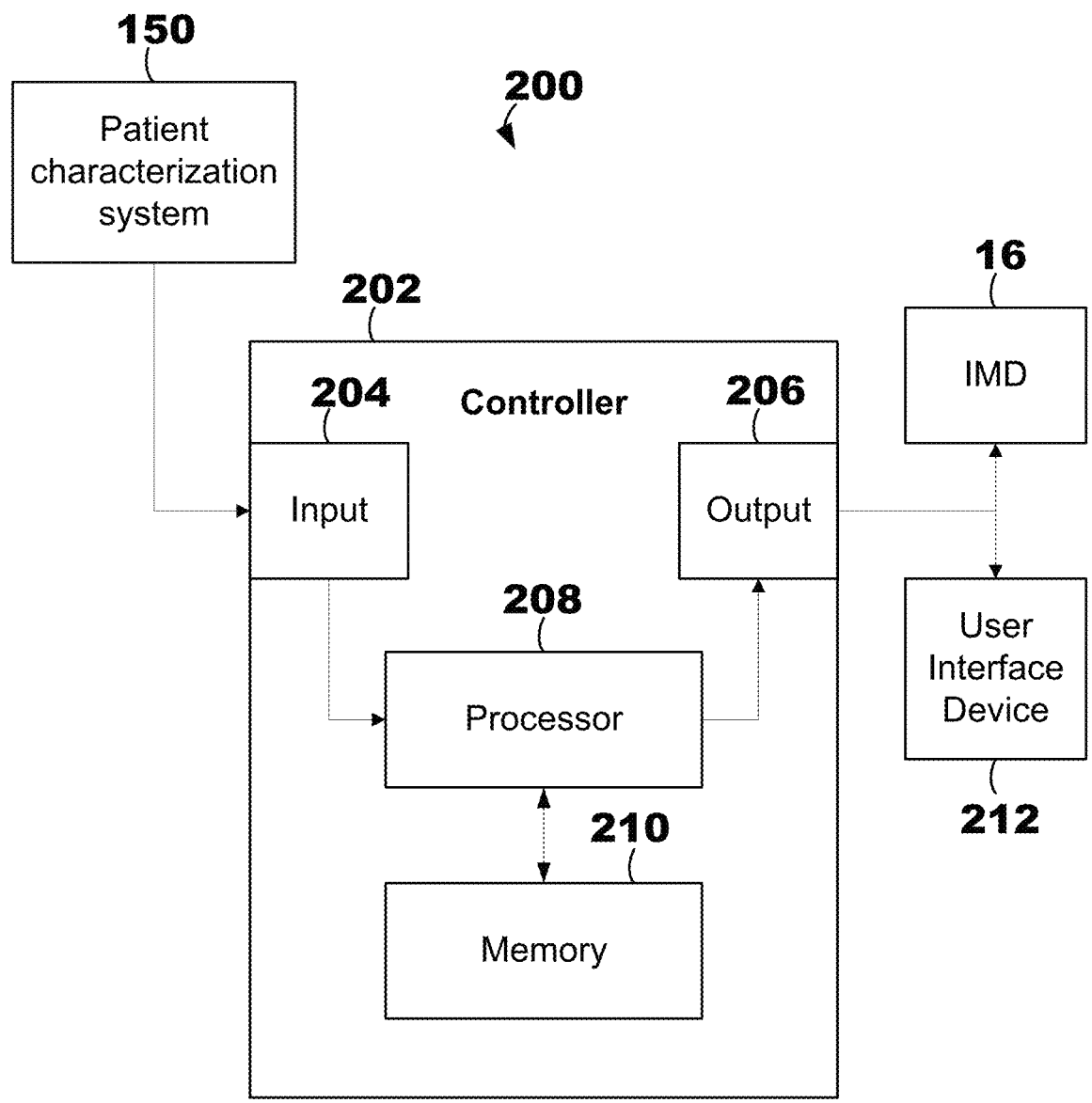
FIG. 5 is a conceptual diagram that illustrates one example of a controller of the therapy modeling system of FIG. 4.

FIG. 5 is a conceptual diagram that illustrates one example of a controller 202 of the therapy modeling system 200. In the illustrated embodiment, the controller 202 may include an input interface 204, an output interface 206, a processor 208 operably coupled to receive data from the input interface and to provide data to the output interface 206, and a memory 210 operably coupled to send data to and receive data from the processor 208. The input interface 204 may be operably coupled to the patient characterization system 150 (for example, one or more devices of the patient characterization system) to receive patient characterization data. The output interface 206 may be operably coupled to the IMD 16 (FIG. 1) of the therapy delivery system 10 (FIG. 1). The output interface 206 may also be operably coupled to a user interface device 212 of the clinician interface system 130 (FIG. 4). In general, the controller 202 may be used to carry out various functionality of the therapy modeling system 200 described herein.

Although a controller is shown as part of the therapy modeling system 200, part of the controller 202, or another similar controller, may also be described as being included in other devices or systems, such as the user interface device 212, therapy delivery system 10, the clinician interface system 130, or the patient characterization system 150.

In general, one or more data handling components described herein, such as controllers, interfaces, apparatus, devices, and systems, may include a processor, such as a central processing unit (CPU), computer, logic array, or other processing circuitry capable of directing data coming into or out of the respective component. Such components may include memory, processing circuitry, and communication hardware (or interfaces). Such components may include circuitry used to couple various subcomponents together or to other components. The functions of such components may be performed by hardware or processing circuitry that may execute computing instructions stored on a non-transient computer readable storage medium. In view of the above, the functionality described herein may be implemented in any suitable manner known to one skilled in the art having the benefit of the present disclosure.

Figure 6:
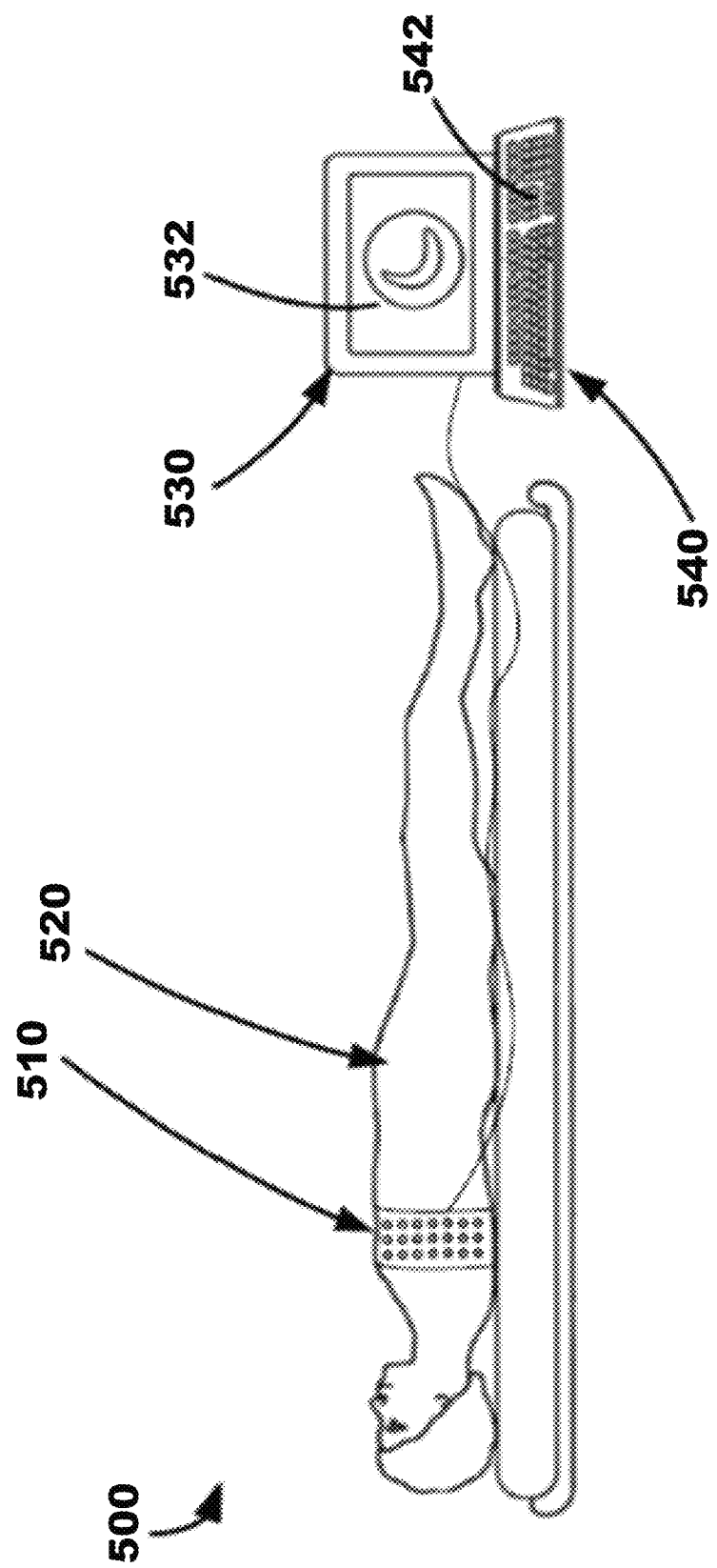
FIG. 6 is a diagram that illustrates an external apparatus including electrode apparatus, display apparatus, and computing apparatus for use in the system of FIG. 1.
Figure 7:
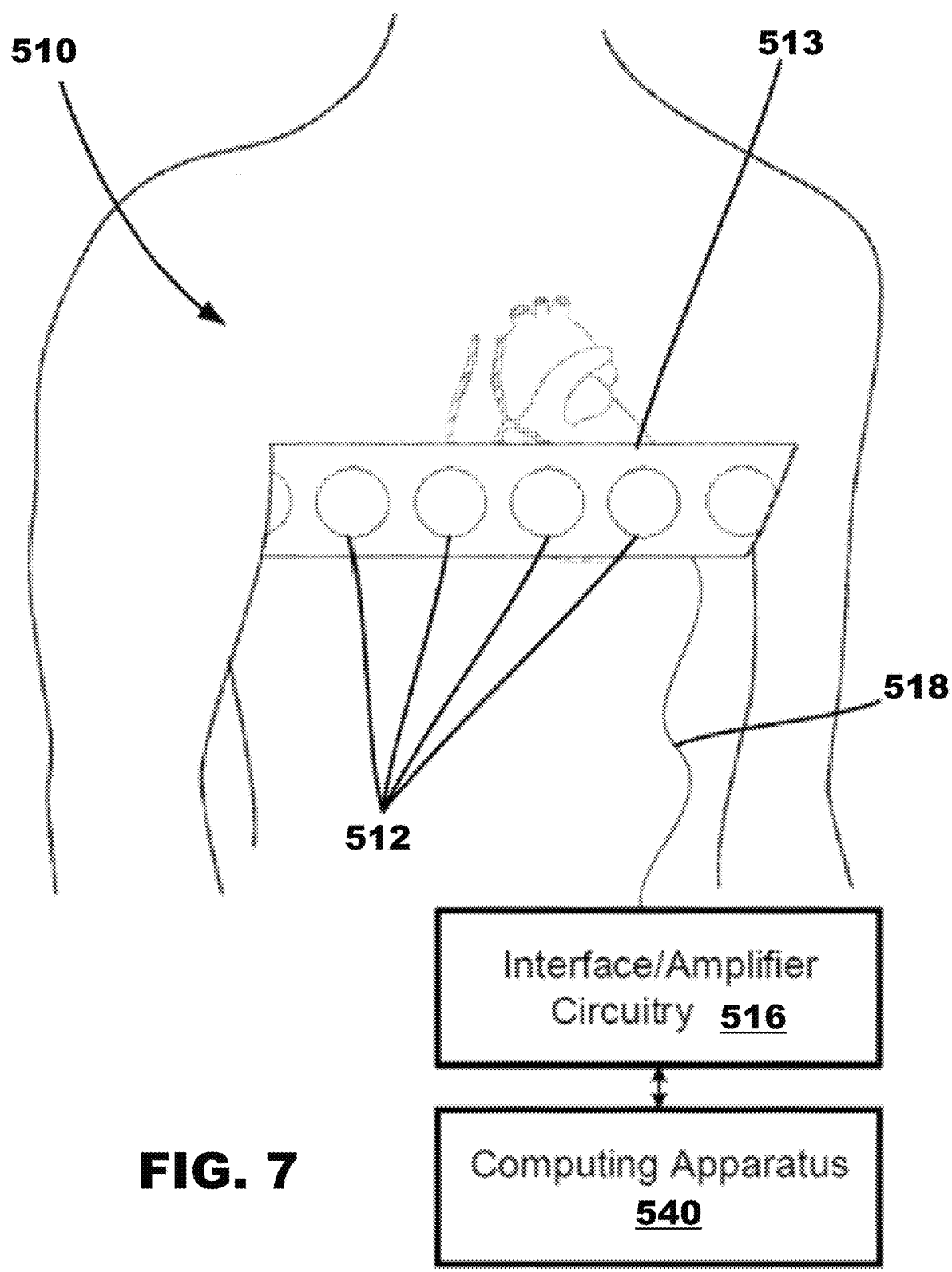
FIGS. 7-8 are diagrams that illustrate two examples of external electrode apparatus for measuring torso-surface potentials for use in the external apparatus of FIG. 6.
Figure 8:
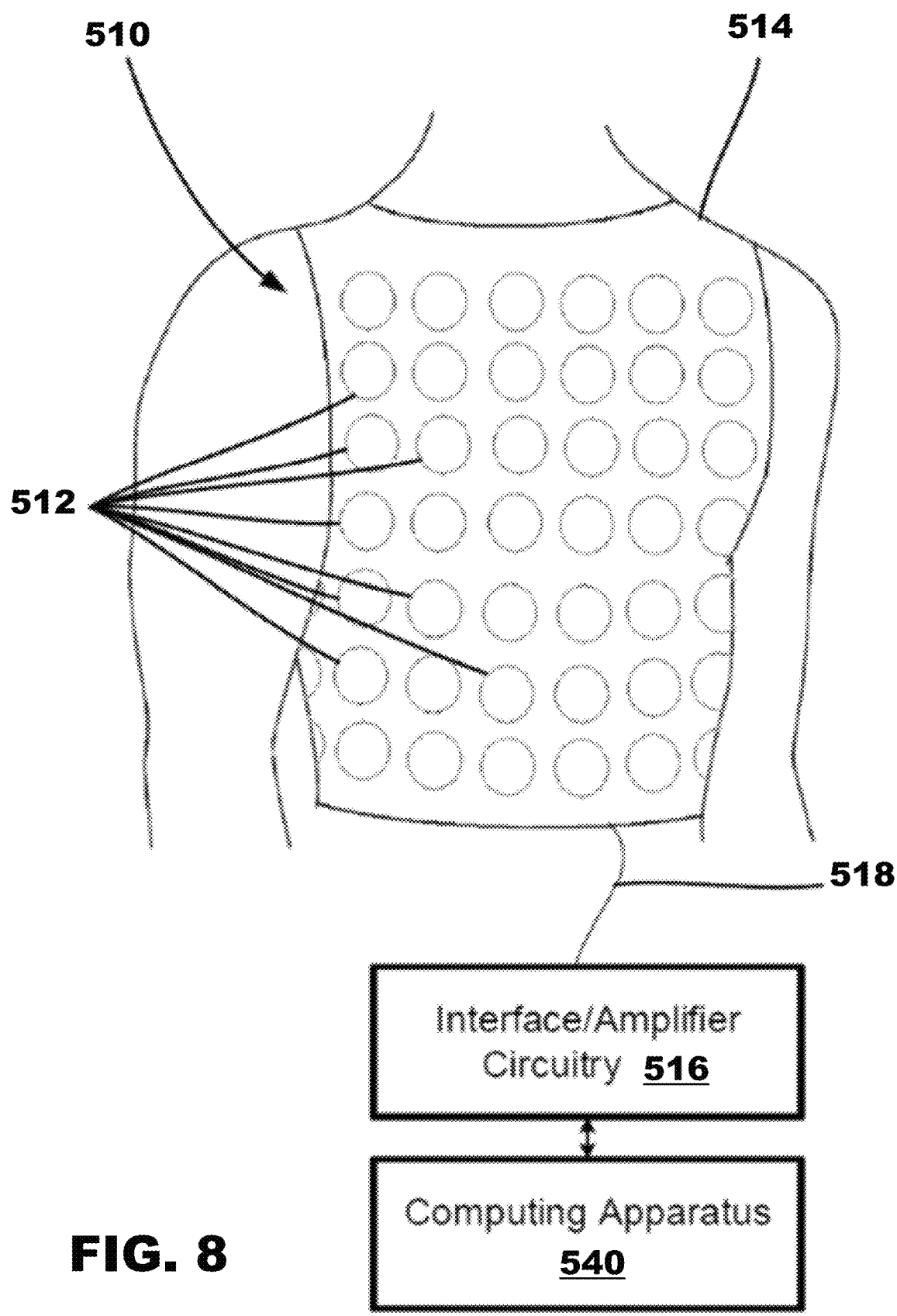

FIGS. 6-8 show examples of external apparatus that may be used to facilitate collecting patient characterization data, such as electrode apparatus data 154 (FIG. 4). FIG. 6 depicts one example of a system 500 of the external apparatus including electrode apparatus 510, display apparatus 530, and computing apparatus 540.

The electrode apparatus 510 as shown includes a plurality of electrodes incorporated, or included, within a band wrapped around the chest, or torso, of a patient 520. The electrode apparatus 510 is operatively coupled to the computing apparatus 540 (for example, through one or wired electrical connections, wirelessly, etc.) to provide electrical signals from each of the electrodes to the computing apparatus 540 for analysis, evaluation, etc. Electrode apparatus may be described in U.S. Pat. No. 9,320,446 entitled "Bioelectric Sensor Device and Methods" and issued on Apr. 26, 2016, which is incorporated herein by reference in its entirety.

Although not described herein, the system 500 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools, such as contrast solution. It is to be understood that the systems, methods, and interfaces described herein may further use imaging apparatus to provide noninvasive assistance to a user (for example, a physician) to calibrate or deliver a cardiac pacing therapy, to locate and position a device to deliver cardiac pacing therapy, or to locate or select a pacing electrode or pacing vector proximate the patient's heart for cardiac pacing therapy in conjunction with the evaluation of cardiac pacing therapy.

For example, the systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a paced setting is optimal or determining whether one or more selected parameters are optimal, such as selected location information (for example, location information for the electrodes to target a particular location in the left ventricle). Systems and methods that use imaging apparatus or electrode apparatus may be described in U.S. Pat. No. 9,877,789 issued on Jan. 30, 2018, and entitled "Implantable Electrode Location Selection," U.S. Pat. No. 10,251,555 issued Apr. 9, 2019, and entitled "Implantable Electrode Location Selection," U.S. Pat. No. 9,924,884 issued on Mar. 27, 2018, and entitled "Systems, Methods, and Interfaces for Identifying Effective Electrodes," U.S. Pat. No. 10,064,567 issued on Sep. 4, 2018, and entitled "Systems, Methods, and Interfaces for Identifying Optical-Electrical Vectors," each of which is incorporated herein by reference in its entirety.

Imaging apparatus may be configured to capture x-ray images or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MM), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MM, etc. Further, it is to be understood that the imaging apparatus may be configured to capture a plurality of consecutive images (for example, continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, for example, to be used to navigate treatment apparatus proximate target locations (for example, such as locations within the RV or LV) within the heart or other areas of interest.

Systems or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 issued May 20, 2014, to Zarkh et al. U.S. Pat. No. 8,861,830 issued Oct. 14, 2014, to Brada et al., U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 530 and the computing apparatus 540 may be configured to display and analyze data such as, for example, electrical signals (for example, electrocardiogram data), cardiac information representative of one or more of mechanical cardiac functionality and electrical cardiac functionality (for example, mechanical cardiac functionality only, electrical cardiac functionality only, or both mechanical cardiac functionality and electrical cardiac functionality), etc. Cardiac information may include, for example, electrical heterogeneity information or electrical dyssynchrony information, surrogate electrical activation information or data, etc. that is generated using electrical signals gathered, monitored, or collected, using the electrode apparatus 510. The computing apparatus 540 may be a server, a personal computer, or a tablet computer. The computing apparatus 540 may be configured to receive input from input apparatus 542 and transmit output to the display apparatus 530. Further, the computing apparatus 540 may include data storage that may allow for access to processing programs or routines or one or more other types of data, for example, for calibrating or delivering pacing therapy for driving a graphical user interface configured to noninvasively assist a user in targeting placement of a pacing device, or for evaluating pacing therapy at that location (for example, the location of an implantable electrode used for pacing, the location of pacing therapy delivered by a particular pacing vector, etc.).

The computing apparatus 540 may be operatively coupled to the input apparatus 542 and the display apparatus 530 to, for example, transmit data to and from each of the input apparatus 542 and the display apparatus 530. For example, the computing apparatus 540 may be electrically coupled to each of the input apparatus 542 and the display apparatus 530 using, for example, analog electrical connections, digital electrical connections, wireless connections, bus-based connections, network-based connections, internet-based connections, etc. As described further herein, a user may provide input to the input apparatus 542 to manipulate, or modify, one or more graphical depictions displayed on the display apparatus 530 and to view or select one or more pieces of information related to the cardiac therapy.

Although as depicted the input apparatus 542 is a keyboard, it is to be understood that the input apparatus 542 may include any apparatus capable of providing input to the computing apparatus 540 for performing the functionality, methods, or logic described herein. For example, the input apparatus 542 may include a mouse, a trackball, a touchscreen (for example, capacitive touchscreen, a resistive touchscreen, a multi-touch touchscreen, etc.), etc. Likewise, the display apparatus 530 may include any apparatus capable of displaying information to a user, such as a graphical user interface 532 including cardiac information, textual instructions, graphical depictions of electrical activation information, graphical depictions of anatomy of a human heart, images or graphical depictions of the patient's heart, graphical depictions of a leadless pacing device used to calibrate or deliver pacing therapy, graphical depictions of a leadless pacing device being positioned or placed to provide cardiac pacing therapy, graphical depictions of locations of one or more electrodes, graphical depictions of a human torso, images or graphical depictions of the patient's torso, graphical depictions or actual images of implanted electrodes or leads, etc. Further, the display apparatus 530 may include a liquid crystal display, an organic light-emitting diode screen, a touchscreen, a cathode ray tube display, etc.

The processing programs or routines stored or executed by the computing apparatus 540 may include programs or routines for computational mathematics, matrix mathematics, dispersion determinations (for example, standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (for example, data compression algorithms), calibration algorithms, image construction algorithms, signal processing algorithms (for example, various filtering algorithms, Fourier transforms, fast Fourier transforms, etc.), standardization algorithms, comparison algorithms, vector mathematics, or any other processing required to implement one or more methods or processes described herein. Data stored or used by the computing apparatus 540 may include, for example, electrical signal/waveform data from the electrode apparatus 510, dispersions signals, windowed dispersions signals, parts or portions of various signals, electrical activation times from the electrode apparatus 510, graphics (for example, graphical elements, icons, buttons, windows, dialogs, pull-down menus, graphic areas, graphic regions, 3D graphics, etc.), graphical user interfaces, results from one or more processing programs or routines employed according to the disclosure herein (for example, electrical signals, cardiac information, etc.), or any other data that may be necessary for carrying out the one or more processes or methods described herein.

Electrical activation times of the patient's heart may be useful to evaluate a patient's cardiac condition or to calibrate, deliver, or evaluate cardiac therapy to be or being delivered to a patient. Surrogate electrical activation information or data of one or more regions of a patient's heart may be monitored, or determined, using electrode apparatus 510 as shown in FIGS. 6-8. The electrode apparatus 510 may be configured to measure body-surface potentials of a patient 520 and, more particularly, torso-surface potentials of the patient 520.

As shown in FIG. 7, the electrode apparatus 510 may include a set, or array, of electrodes 512, a strap 513, and interface/amplifier circuitry 516. A portion of the set of electrodes may be used wherein the portion corresponds to a particular location on the patient's heart. The electrodes 512 may be attached, or coupled, to the strap 513, and the strap 513 may be configured to be wrapped around the torso of a patient 520 such that the electrodes 512 surround the patient's heart. As further illustrated, the electrodes 512 may be positioned around the circumference of a patient 520, including the posterior, lateral, posterolateral, anterolateral, and anterior locations of the torso of a patient 520.

Further, the electrodes 512 may be electrically connected to interface/amplifier circuitry 516 via wired connection 518. The interface/amplifier circuitry 516 may be configured to amplify the signals from the electrodes 512 and provide the signals to the computing apparatus 540. Other systems may use a wireless connection to transmit the signals sensed by electrodes 512 to the interface/amplifier circuitry 516 and, in turn, the computing apparatus 540, for example, as channels of data. For example, the interface/amplifier circuitry 516 may be electrically coupled to each of the computing apparatus 540 and the display apparatus 530 using, for example, analog electrical connections, digital electrical connections, wireless connections, bus-based connections, network-based connections, internet-based connections, etc.

Although in the example of FIG. 7 the electrode apparatus 510 includes a strap 513, in other examples any of a variety of mechanisms, for example, tape or adhesives, may be employed to aid in the spacing and placement of electrodes 512. In some examples, the strap 513 may include an elastic band, strip of tape, or cloth. In other examples, the electrodes 512 may be placed individually on the torso of a patient 520. Further, in other examples, electrodes 512 (for example, arranged in an array) may be part of, or located within, patches, vests, or other manners of securing the electrodes 512 to the torso of the patient 520.

The electrodes 512 may be configured to surround the heart of the patient 520 and record, or monitor, the electrical signals associated with the depolarization and repolarization of the heart after the signals have propagated through the torso of a patient 520. Each of the electrodes 512 may be used in a unipolar configuration to sense the torso-surface potentials that reflect the cardiac signals. The interface/amplifier circuitry 516 may also be coupled to a return or indifferent electrode (not shown) that may be used in combination with each electrode 512 for unipolar sensing. In some examples, there may be about 12 to about 50 electrodes 512 spatially distributed around the torso of the patient. Other configurations may have more or fewer electrodes 512.

The computing apparatus 540 may record and analyze the electrical activity (for example, torso-surface potential signals) sensed by electrodes 512 and amplified/conditioned by the interface/amplifier circuitry 516. The computing apparatus 540 may be configured to analyze the signals from the electrodes 512 to provide as anterior and posterior electrode signals and surrogate cardiac electrical activation times, for example, representative of actual, or local, electrical activation times of one or more regions of the patient's heart as will be further described herein. The computing apparatus 540 may be configured to analyze the signals from the electrodes 512 to provide as anterior-septal electrode signals and surrogate cardiac electrical activation times, for example, representative of actual, or local, electrical activation times of one or more anterior-septal regions of the patient's heart, as will be further described herein, for example, for use in calibrating, delivering, or evaluating pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. Measurement of activation times can be performed by measuring the period of time between an onset of cardiac depolarization (for example, onset of QRS complex) and an appropriate fiducial point such as, for example, a peak value, a minimum value, a minimum slope, a maximum slope, a zero crossing, a threshold crossing, etc.

Additionally, the computing apparatus 540 may be configured to provide graphical user interfaces depicting the surrogate electrical activation times obtained using the electrode apparatus 510. Systems, methods, or interfaces may noninvasively use the electrical information collected using the electrode apparatus 510 to evaluate a patient's cardiac condition or to calibrate, deliver, or evaluate cardiac pacing therapy to be or being delivered to the patient.

FIG. 8 illustrates another electrode apparatus 510 that includes a plurality of electrodes 512 configured to surround the heart of the patient 520 and record, or monitor, the electrical signals associated with the depolarization and repolarization of the heart after the signals have propagated through the torso of the patient 520. The electrode apparatus 510 may include a vest 514 upon which the plurality of electrodes 512 may be attached, or to which the electrodes 512 may be coupled. The plurality, or array, of electrodes 512 may be used to collect electrical information such as, for example, surrogate electrical activation times.

Similar to the electrode apparatus 510 of FIG. 7, the electrode apparatus 510 of FIG. 8 may include interface/amplifier circuitry 516 electrically coupled to each of the electrodes 512 through a wired connection 518 and be configured to transmit signals from the electrodes 512 to computing apparatus 540. As illustrated, the electrodes 512 may be distributed over the torso of a patient 520, including, for example, the anterior, lateral, posterolateral, anterolateral, and posterior surfaces of the torso of the patient 520.

The vest 514 may be formed of fabric with the electrodes 512 attached to the fabric. The vest 514 may be configured to maintain the position and spacing of electrodes 512 on the torso of the patient 520. Further, the vest 514 may be marked to assist in determining the location of the electrodes 512 on the surface of the torso of the patient 520. The vest 514 may include about 17 or more anterior electrodes positionable proximate the anterior torso of the patient, and about 39 or more posterior electrodes positionable proximate the posterior torso of the patient. In some examples, there may be about 25 electrodes 512 to about 256 electrodes 512 distributed around the torso of the patient 520, though other configurations may have more or fewer electrodes 512.

As described herein, the electrode apparatus 510 may be configured to measure electrical information (for example, electrical signals) representing different regions of a patient's heart. For example, activation times of different regions of a patient's heart can be approximated from surface ECG activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 512, and not the entire set, can be used to generate activation times corresponding to a particular location of the patient's heart that the portion of the set of electrodes corresponds to.

The systems, methods, and interfaces may be used to provide noninvasive assistance to a user in the evaluation of a patient's cardiac health or status, or the evaluation of cardiac therapy, such as HFpEF therapy, by use of the electrode apparatus 510 (for example, cardiac therapy being presently-delivered to a patient during implantation or after implantation). Further, the systems, methods, and interfaces may be used to assist a user in the configuration, or calibration, of the cardiac therapy, such as CRT, to be or being delivered to a patient.

Electrical activity may be monitored using a plurality of external electrodes, such as electrodes 512 of FIGS. 6-8. The electrical activity can be monitored by a plurality of electrodes during pacing therapy or in the absence of pacing therapy. The monitored electrical activity can be used to evaluate pacing therapy to a patient. The electrical activity monitored using the ECG belt described can be used to evaluate at least one paced setting of the pacing therapy on the heart. As an example, a paced setting can be any one parameter or a combination of parameters including, but not limited to, electrode position, pacing polarity, pacing output, pacing pulse width, timing at which ventricular pacing is delivered relative to atrial timing, pacing rate, etc. Further, as an example, the location of the leadless device or a pacing lead can include a location in the right ventricle, left ventricle, or right atrium.

Further, body-surface isochronal maps of ventricular activation can be constructed using the monitored electrical activity during pacing therapy or in the absence of pacing therapy. The monitored electrical activity or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (for example, standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of pacing therapy at one or more paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In another example, only ASAT may be determined and further used, or ASAT may be more heavily weighted than other values.

One or more paced settings associated with the pacing therapy may be evaluated. A paced setting can include a plurality of pacing parameters. The plurality of pacing parameters can be optimal if the patient's cardiac condition improves, if the pacing therapy is effectively capturing a desired portion of the RA, RV, or LV, or if a metric of electrical heterogeneity improves by a certain threshold compared to a baseline rhythm or therapy. The determination of whether the paced setting is optimal can be based on at least one metric of electrical heterogeneity generated from electrical activity during pacing (and also, in some cases, during native conduction, or in the absence of pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, or if the location of the pacing therapy to excite the left ventricle causes a particular pattern of excitation of the muscle fibers in the heart. In addition, the plurality of pacing parameters can be optimal if a metric of electrical heterogeneity indicates a correction of a left bundle branch block (LBBB), or if a metric of electrical heterogeneity indicates a complete engagement of a Purkinje system, etc. As an example, a metric of electrical heterogeneity of an ASAT less than or equal to a threshold (for example, a threshold of 30 ms) and an LVAT less than or equal to a threshold (for example, a threshold of 30 ms) can indicate a correction of an LBBB, and thus, the paced setting is optimal. As an example, a metric of electrical heterogeneity of an RVAT less than or equal to a threshold (for example, a threshold of 30 ms), an ASAT less than or equal to a threshold (for example, a threshold of 30 ms), and an LVAT less than or equal to a threshold (for example, a threshold of 30 ms) can indicate a complete engagement of the Purkinje system, and thus the paced setting is may be optimal.

The paced setting can be determined to be optimal in response to the pacing therapy using the paced setting being acceptable, being beneficial, being indicative of complete engagement of patient's native cardiac conduction system, being indicative of correction of a ventricular conduction disorder (for example, left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, or a pacing location, etc. A pacing vector can include any two or more pacing electrodes such as, for example, a tip electrode to a can electrode, a tip electrode to a ring electrode etc., that are used to deliver the pacing therapy, etc. The pacing location can refer to the location of any of the one or more pacing electrodes that are positioned using a lead, a leadless device, or any device or apparatus configured to deliver pacing therapy.

A paced setting for therapy may be adjusted. The paced setting can be adjusted in response to the paced setting being not optimal. The paced setting can be adjusted in response to the paced setting being within an optimal range but in order to determine whether the paced setting can be at a position within the optimal range that is more beneficial, more useful, more functional, etc., for the pacing therapy. The paced setting could be adjusted to find the most optimal metric of electrical heterogeneity.

A determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

Figure 9:
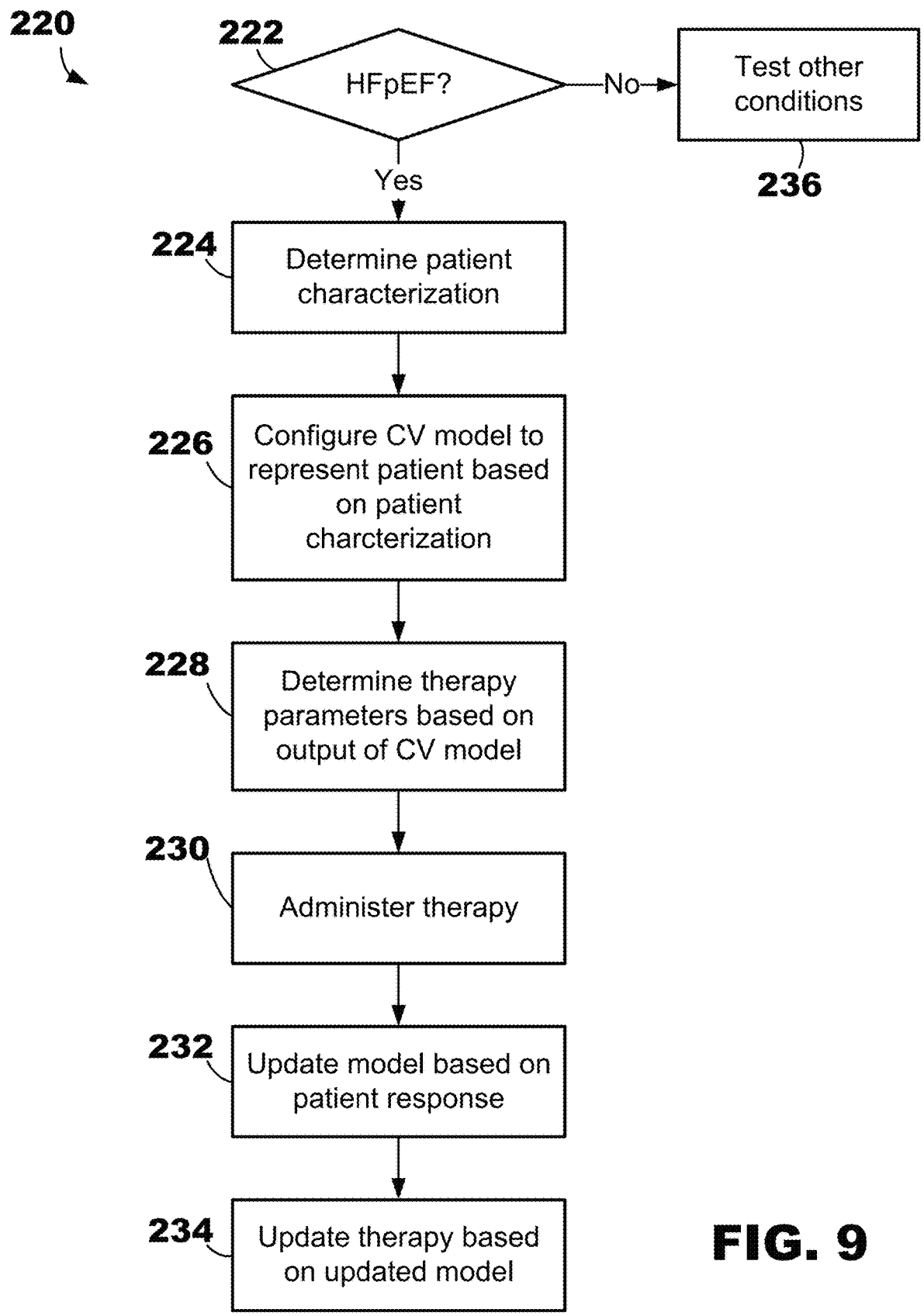
FIG. 9 is a flow diagram that illustrates one example of a method usable with the therapy modeling system of FIG. 4.

FIG. 9 is a flow diagram that illustrates one example of a method that may be used with the therapy modeling system 200 (FIG. 4) to manage therapy, such as HFpEF therapy. As illustrated, the method 220 may include determining whether a patient has HFpEF 222. The HFpEF classification, or diagnosis, may be made by the clinician in a clinical setting or may be determined from patient history data. In some embodiments, other conditions may be tested 236, for example, in response to determining that the patient does not have HFpEF 222. The method 220 may continue to manage HFpEF therapy, for example, in response to determining that the patient has HFpEF 222.

A patient characterization may be determined based on patient characterization 224, for example, in response to determining that the patient has HFpEF 222. The patient characterization data 224 may be based on one or more of the following: clinician input data, electrode apparatus data, echocardiogram data, imaging data, patient history data, hemodynamic measurement data, or IMD data.

A CV model of the therapy modeling system 200 may be configured to represent the patient based on the patient characterization 226, for example, in response to determining the patient characterization 224. Any suitable CV model that appropriately characterizes a patient's heart and cardiovascular structure for HF, or specifically HFpEF, may be used. Non-limiting example of CV models include the CircAdapt model (available from Maastricht University of Maastricht, Netherlands), the HARVI model (available from PVLoops LLC of New York, N.Y.), and the CARP model (available from Medical University Graz of Graz, Austria). In general, the CV model may be configured using some or all the patient characterization data described herein and provide output data. The output data may include various parameters representing a simulated response of the patient's heart.

One or more therapy parameters may be determined based on output data from the CV model 228, for example, in response to configuring the CV model 226. Therapy parameters may include a type of therapy or particular parameters used to configure a particular therapy. In some embodiments, determining a type of therapy may include determining one or more candidate therapies using the CV model (see FIG. 10). In some embodiments, determining a type of therapy may include determining a non-pacing therapy by a clinician using the CV model (see FIG. 15).

In some embodiments, therapy parameters may be determined for pacing therapy, such as a type of pacing therapy (such as cardiac remodeling pacing therapy, atrial resynchronization therapy, cardiac resynchronization therapy, or ventricular resynchronization therapy), a pacing rate, a sensing or pacing location, a pacing duration, a pacing duty cycle, or a pacing frequency. Pacing therapy may be administered using an IMD, such as IMD 16 (FIG. 1). A sensing or pacing location may be indicative of an atrial location, a ventricular location, or a conduction system or His bundle location. A pacing duration, duty cycle, and frequency may be used together to indicate, for example, five hours of continuous pacing daily, intermittent with 10 minute duration and 20 minute duty cycle.

Therapy may be administered based on the one or more therapy parameters 230, for example, in response to determining the one or more therapy parameters 228. In some embodiments, administering therapy may include configuring an IMD and administering pacing therapy using the 1 MB. Additionally, or alternatively, in some embodiments, administering therapy may include administering non-pacing therapy by a clinician. For example, in some embodiments, administering the non-pacing therapy may include providing the one or more therapy parameters for non-pacing therapy to the clinician on a user interface device. The clinician may provide the non-pacing therapy to the patient, such as a surgical procedure.

The CV model may be updated, for example, based on the patient's response 232, for example, in response to administering therapy 230. In some embodiments, patient response data may be provided, for example, from the clinician or from the IMD, as patient characterization data to the therapy modeling system 200. The model may be reconfigured based on the patient response data, which may also be described as updated patient characterization data.

In some embodiments, the therapy modeling system 200 may be described as providing continuous therapy optimization using model predictions based on changes (reinforcement learning techniques). In some embodiments, the CV model may be updated based on a predicted patient characterization value and a measured patient characterization value after administering HFpEF therapy. For example, the predicted patient characterization value may be generated based on the output data of the CV model. The patient characterization system 150 (FIG. 4) or the therapy delivery system 10 (FIG. 4) may be used to measure a patient characterization value after administering HFpEF therapy, for example, after a period of time. The predicted and measured patient characterization values may be compared and used as feedback to update the CV model to facilitate future predictive accuracy.

The therapy may be updated based on output data 234 from the updated (or reconfigured) CV model, for example, in response to updating the CV model 232. In some embodiments, the therapy may be updated in a clinical setting or updated remotely, for example, over an internet connection between the IMD of the therapy delivery system and the therapy modeling system 200.

In some embodiments, the CV model or the therapy may be updated over the internet. Patient response data may be determined based on updated patient characterization data, for example, measured using an implantable medical device (IMD). The updated patient characterization data may be provided over the internet to a remote therapy modeling system 200. The CV model may be executed by processing circuitry of the remote therapy modeling system 200.

In some embodiments, the therapy modeling system 200 may be described as providing ambulatory updates over the internet. Updates from the therapy delivery system 10 may be used as feedback to the CV model to drive continuous optimization. For example, an impedance change indicating an expansion of the ventricular volume may reach or exceed a corresponding threshold. The therapy delivery system 10 may trigger a transmission, or periodically send a transmission, to the therapy modeling system 200, and the CV model may be automatically updated and run by the therapy management system. A recommendation, or an automated update, may be made regarding the pacing rate to preserve a target cardiac volume without additional expansion, which may be provided by the therapy modeling system 200 to the clinician interface system 130 (FIG. 4) or the therapy delivery system 10.

In one example of using the therapy modeling system 200 for pacing therapy, the method 220 may include determining a characterization by classification of a patient, such as a cohort or micro-cohort for the particular patient. The cohort or micro-cohort may be determined, for example, based in physician input from a clinical exam or from patient history data. Individual patient data may or may not be used in addition to the classification. The CV model may be configured based on the particular patient cohort or micro-cohort. One or more candidate therapies may be determined, or tested, using the CV model (see FIG. 10). In particular, pacing therapy by an IMD may be tested with one or more test therapy parameters using the CV model to provide output data indicating a simulated patient response. The candidate therapies may include any suitable therapy, such as HFpEF therapy, or enabling therapy. Enabling therapy may be described as therapy that enables effective treatment using another therapy (see FIG. 17). One or more therapy parameters, which may include a selected therapy, may be determined based on the output data from the CV model. The one or more therapy parameters may also be determined based on clinician input, for example, to configure the CV model, to run tests using the CV model, or after receiving output data from the CV model. An IMD may be selected and configured based on the one or more therapy parameters, and the configured IMD may be used to administer pacing therapy.

Figure 10:
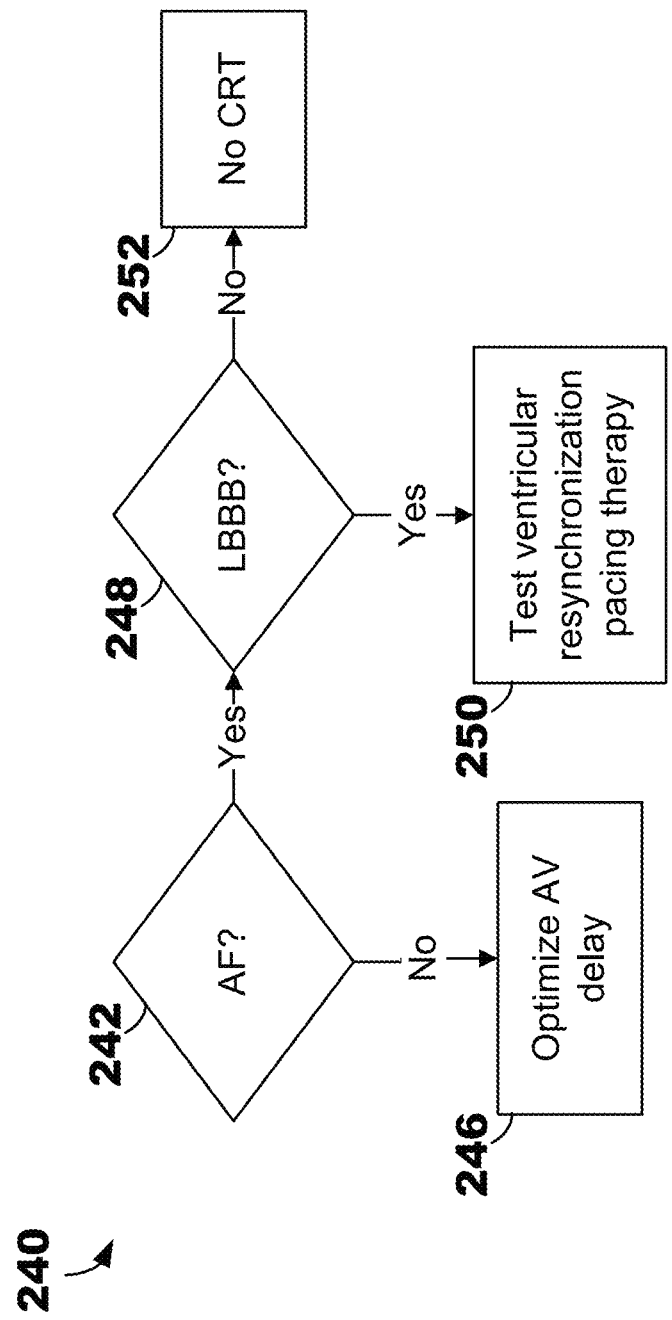
FIG. 10 is a flow diagram that illustrates one example of a method for determining one or more candidate therapies usable with the therapy modeling system of FIG. 4.

FIG. 10 is a flow diagram that illustrates one example of a method 240 for determining one or more candidate therapies using the CV model, which may be used, for example, in configuring the CV model 226 (FIG. 6) and determining the one or more therapy parameters 228 (FIG. 6). The method 240 may include determining whether the patient has atrial fibrillation (AF) 242. An AF classification may be determined based on patient characterization data, such as electrode apparatus data from an ECG, ECG belt, or ECG vest or patient history data indicating AF. The AF classification may be used to configure the CV model.

An atrioventricular (AV) delay for pacing therapy may be optimized 246, for example, in response to determining that the patient does not have AF 242. Any suitable technique may be used to optimize AV delay (for example, see FIG. 11). In general, optimizing the AV delay may include testing a plurality of different pacing therapies to identify acceptable AV delays using the CV model. The CV model may be configured for a patient having HFpEF without AF. Optimizing the AV delay may be used to determine one or more therapy parameters.

Determining whether the patient has a left bundle branch block (LBBB) 248 may be determined, for example, in response to determining that the patient has AF 242. An LBBB classification may be determined based on patient characterization data, such as electrode apparatus data from an ECG, ECG belt, or ECG vest or patient history data indicating an LBBB. The LBBB classification may be used to configure the CV model.

Ventricular resynchronization pacing therapy may be tested 250, for example, in response to determining that the patient has an LBBB 248. Any suitable technique may be used to test ventricular resynchronization pacing therapy (for example, see FIG. 12). The CV model may be configured for a patient having AF and an LBBB. Testing ventricular resynchronization pacing therapy may be used to determine one or more therapy parameters.

One or more therapy parameters may be determined to not provide CRT 252, for example, in response to determining that the patient does not have an LBBB 248. In some embodiments, other therapies, such as RBBB pacing therapy or non-specific intraventricular delay pacing therapy, may be provided.

Figure 11:
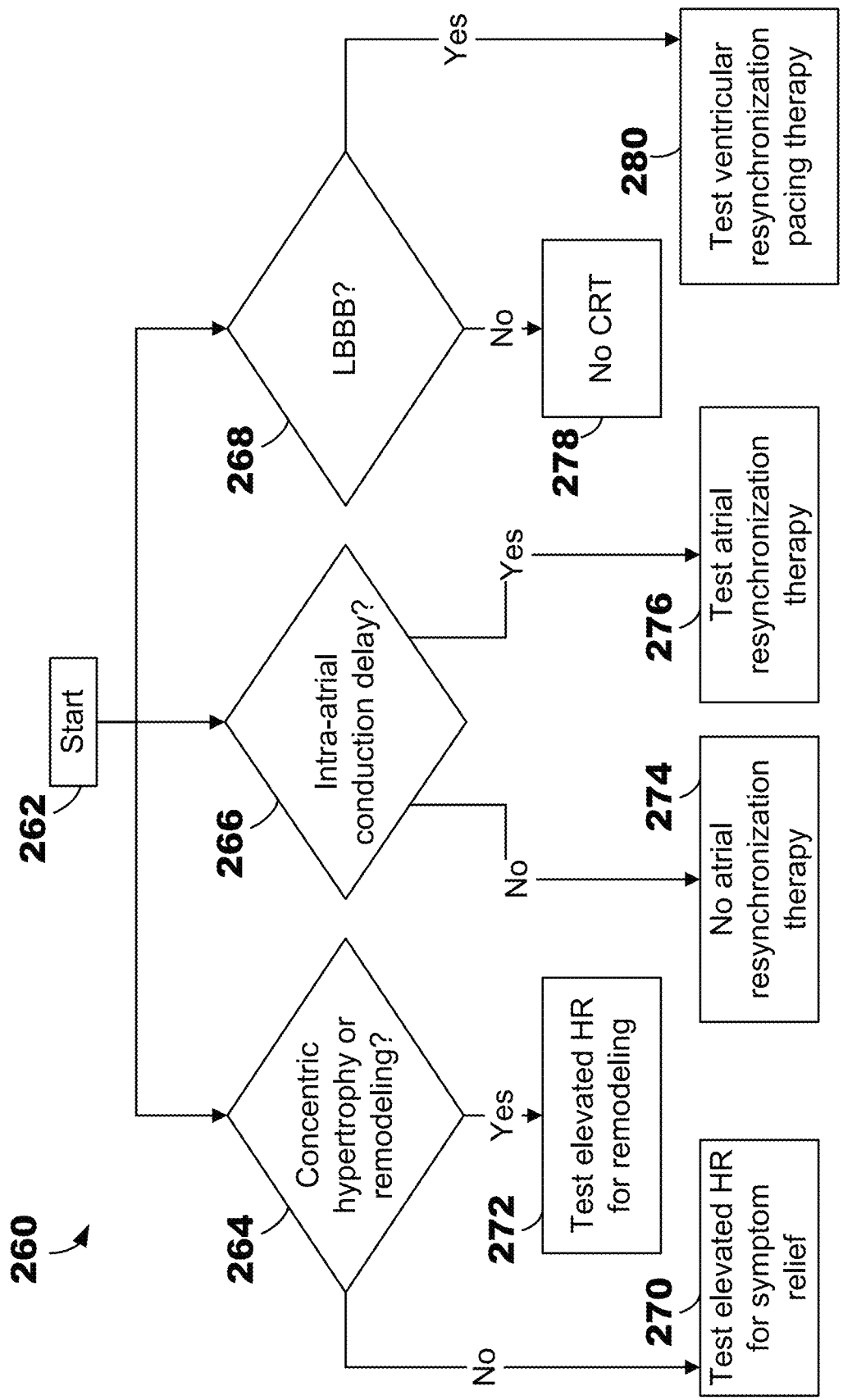
FIG. 11 is a flow diagram that illustrates one example of a method for testing a plurality of different pacing therapies usable with the therapy modeling system of FIG. 4.

FIG. 11 is a flow diagram that illustrates one example of a method 260 for testing a plurality of different pacing therapies to identify acceptable AV delays using the CV model, which may be used in optimizing the AV delay 246 (FIG. 10). The method 260 may start 262 by determining one or more classifications of the patient, such as one or more of determining whether the patient has concentric hypertrophy or concentric remodeling 264, determining whether the patient has an intra-atrial conduction delay 266, or determining whether the patient has an LBBB 268. In general, the CV model may be configured before testing in the method 260 to represent a patient that has HFpEF and does not have AF.

Whether the patient has concentric hypertrophy or concentric remodeling 264 may be determined, for example, using echocardiogram data or other imaging data. The CV model may be further configured based on whether the patient has concentric hypertrophy or concentric remodeling.

The method 260 may include testing an elevated HR pacing therapy for symptom relief 270, for example, in response to determining that the patient does not have concentric hypertrophy or concentric remodeling 264. The CV model may be further configured before testing to represent a patient that does not have concentric hypertrophy or concentric remodeling.

The method 260 may include testing an elevated HR pacing therapy for remodeling 272, for example, in response to determining that the patient has concentric hypertrophy or concentric remodeling 264. The CV model may be further configured before testing to represent a patient that has concentric hypertrophy or concentric remodeling.

In general, the elevated HR pacing therapy for remodeling may include one or more HR pacing rates that are higher than the elevated HR pacing therapy for symptom relief. The elevated HR pacing therapy for symptom relief may be described as a "mild" elevated, or increased, HR pacing therapy, which is intended to not to lead to remodeling. The elevated pacing therapy for remodeling may be described as an "aggressive" elevated, or increased, HR pacing therapy, which may be intended to lead to remodeling.

Whether the patient has an intra-atrial conduction delay 266 may be determined, for example, based on electrode apparatus data from an ECG, ECG belt, or ECG vest. The CV model may be further configured based on whether the patient has an intra-atrial conduction delay.

The method 260 may include determining one or more therapy parameters to provide no atrial resynchronization therapy 274 or determining to not test atrial resynchronization therapy, for example, in response to determining that the patient does not have an intra-atrial conduction delay 266.

The method 260 may include testing atrial resynchronization therapy 276, for example, in response to determining that the patient has an intra-atrial conduction delay 266. The CV model may be further configured before testing to represent a patient that has an intra-atrial conduction delay. Testing an intra-atrial conduction delay 276 may include one or more of the following: testing Bachmann's bundle pacing, testing biatrial pacing (RA-LA pacing), or testing left atrial fusion pacing (LA pacing triggered by right atrial sensing).

Whether the patient has an LBBB 268 may be determined, for example, using electrode apparatus data from an ECG, ECG belt, or ECG vest. The CV model may be further configured based on whether the patient has an LBBB.

The method 260 may include determining one or more therapy parameters to not provide CRT 278 or determining not to test ventricular resynchronization pacing therapy, for example, in response to determining that the patient does not have an LBBB 268.

The method 260 may include testing ventricular resynchronization pacing therapy 280, for example, in response to determining that the patient has an LBBB 268. The CV model may be further configured before testing to represent a patient that has an LBBB. Testing ventricular resynchronization pacing therapy 280 may include one or more of the following: testing left bundle branch (LBB) pacing, testing His bundle pacing, testing left ventricular pacing (such as LV myocardial pacing, or testing bi-ventricular pacing.

After testing various different pacing therapies, one of the pacing therapies having acceptable AV delays may be selected. For example, acceptable AV delays may be determined using a range of acceptable AV delay thresholds. Any suitable technique may be used to determine an acceptable AV delay known to one skilled in the art having the benefit of this disclosure.

Figure 12:
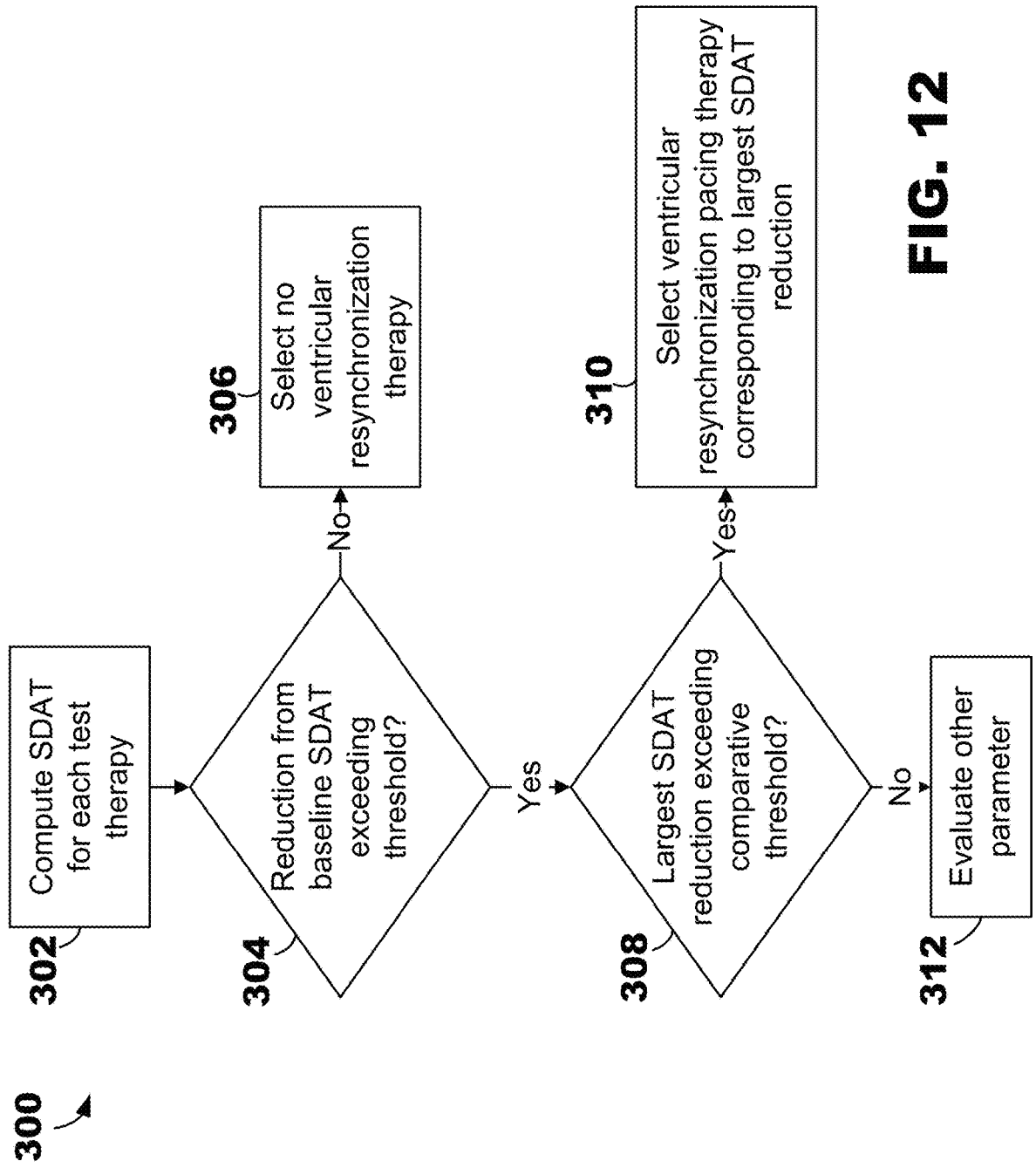
FIG. 12 is a flow diagram that illustrates one example of a method for testing ventricular resynchronization pacing therapy usable with the therapy modeling system of FIG. 4.

FIG. 12 is a flow diagram that illustrates one example of a method 300 for testing ventricular resynchronization pacing therapy, which may be used in test 250 (FIG. 10) or in test 280 to optimize the AV delay 260 (FIG. 11). The method 300 may include determining a plurality of cardiac dyssynchrony measure values using the CV model 302. Each measure value may correspond to a different test ventricular resynchronization therapy of a plurality of test ventricular resynchronization pacing therapies. One example of a cardiac dyssynchrony measure is SDAT. In the illustrated embodiment, for example, an SDAT may be determined for each CRT, such as ventricular resynchronization pacing therapy, being tested.

The method 300 may include determining whether any of the cardiac dyssynchrony measure values indicate a reduction from a baseline patient cardiac dyssynchrony measure value greater than or equal to a reduction threshold 304. Non-limiting examples of reduction thresholds include 5, 10, 15, or 20 percent. In some embodiments, a reduction threshold of 10 percent may be used. In some embodiments, the reduction threshold may be determined based on SDAT measure values.

The method 300 may also include determining (or selecting) to provide one or more therapy parameters to provide no ventricular resynchronization pacing therapy 306, for example, in response to determining that none of the cardiac dyssynchrony measure values indicate a reduction of greater than the reduction threshold 304.

The method 300 may include determining a largest reduction cardiac dyssynchrony measure value corresponding to a largest reduction in cardiac dyssynchrony from the baseline patient cardiac dyssynchrony measure value, for example, in response to determining that at least one of the cardiac dyssynchrony measure values indicates a reduction greater than or equal to the reduction threshold 304. The method 300 may also include determining whether the largest reduction cardiac dyssynchrony measure value is greater than the other cardiac dyssynchrony measure values by at least a comparative threshold 308. Non-limiting examples of comparative thresholds include 1, 2, 3, 4, 5, 6, 7, 8, 9, or 10 basis points of the particular cardiac dyssynchrony measure, such as SDAT. In some embodiments, a comparative threshold of 5 basis points for SDAT may be used.

The method 300 may also include determining (or selecting) one or more therapy parameters to provide ventricular resynchronization pacing therapy corresponding to the largest reduction cardiac dyssynchrony measure value 310, for example, in response to determining that that the largest reduction cardiac dyssynchrony measure value is greater than the other cardiac dyssynchrony measure values by at least the comparative threshold 308. In some embodiments, the one or more therapy parameters for ventricular resynchronization pacing therapy may be determined based on the largest SDAT reduction.

The method 300 may include evaluating one or more other patient characterization parameters 312, for example, in response to determining that the largest reduction cardiac dyssynchrony measure value is not greater than the other cardiac dyssynchrony measure values by at least the comparative threshold 308.

Figure 13:
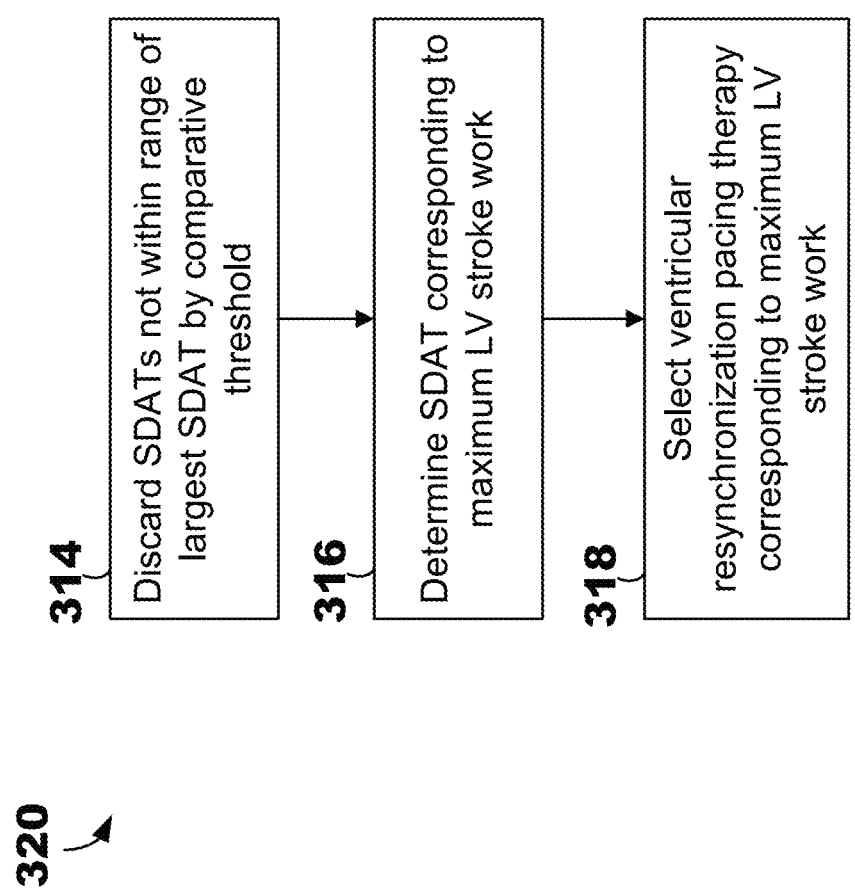
FIG. 13 is a flow diagram that illustrates one example of a method for evaluating one or more other patient characterization parameters usable with the therapy modeling system of FIG. 4.

FIG. 13 is a flow diagram that illustrates one example of a method 320 for evaluating one or more other patient characterization parameters, which may be used in evaluation 312 (FIG. 12). In some embodiments, the method 320 may be used to determine one or more therapy parameters 228 (FIG. 9).

The method 320 may include discarding any cardiac dyssynchrony measure values not within range of the largest reduction cardiac dyssynchrony measure value by the comparative threshold 314, for example, in response to determining that the largest reduction cardiac dyssynchrony measure value is not greater than the other cardiac dyssynchrony measure values by at least the comparative threshold 308 (FIG. 12).

The method 320 may also include determining which of the cardiac dyssynchrony measure values correspond to a maximum LV stroke work using the CV model 316, for example, in response to discarding any cardiac dyssynchrony measure values not within range of the largest reduction cardiac dyssynchrony measure value by the comparative threshold 314. In some embodiments, a maximum cardiac stroke work efficiency may be used in addition to, or as an alternative to, the maximum LV stroke work.

The method 320 may include determining (or selecting) the one or more therapy parameters to provide ventricular resynchronization pacing therapy based on the cardiac dyssynchrony measure value corresponding to the maximum LV stroke work 318, for example, in response to determining which of the cardiac dyssynchrony measure values correspond to a maximum LV stroke work using the CV model 316.

Figure 14:
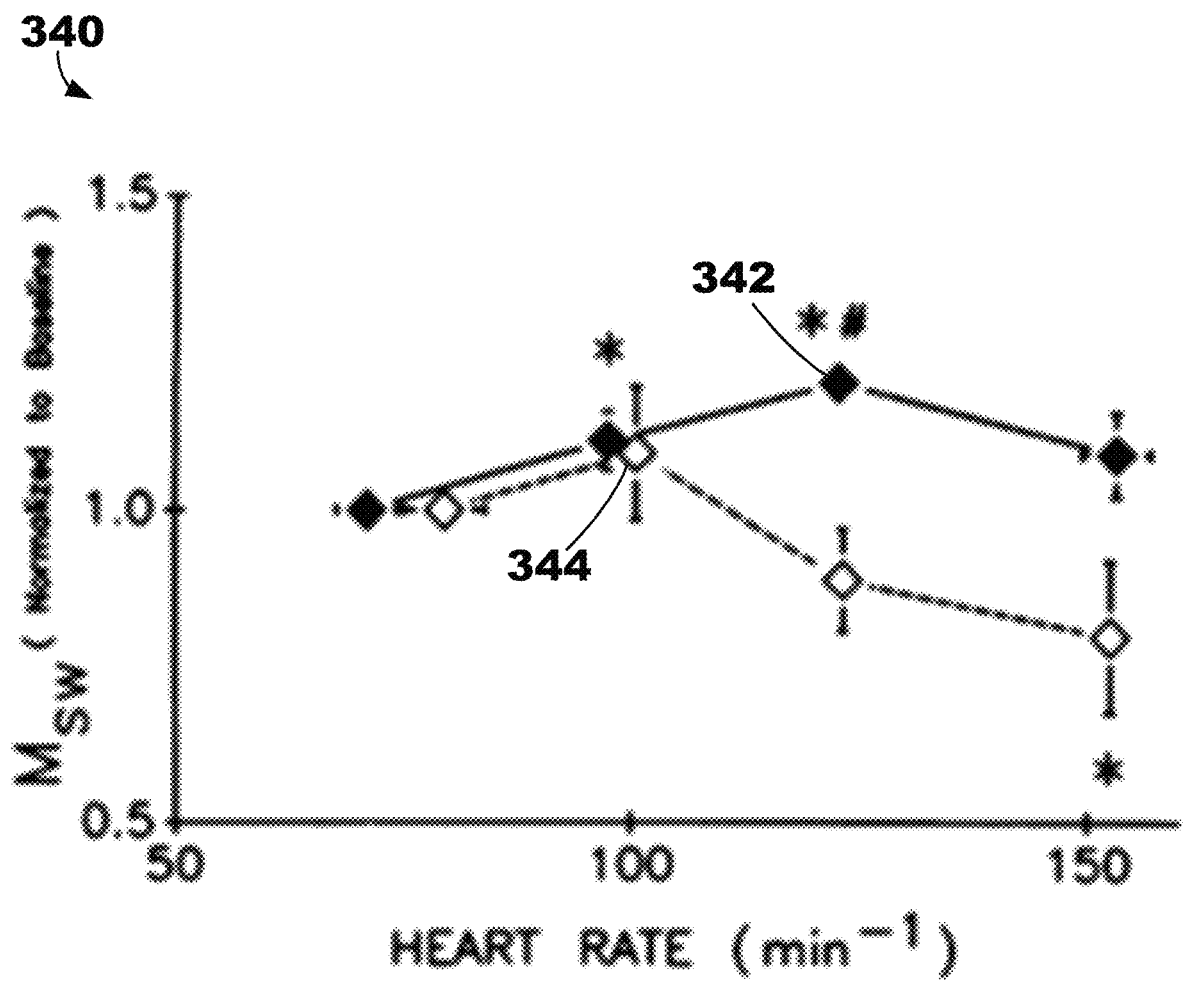
FIG. 14 is a diagram that illustrates one example of a plot of output data from a CV model for therapy optimization usable with the therapy modeling system of FIG. 4.

FIG. 14 is a diagram that illustrates one example of a plot 340 of output data from a CV model, which may be used to determine one or more therapy parameters 228 (FIG. 9). In particular, the plot 340 may be used to predict a patient response to therapy and to evaluate whether certain therapy parameters should be avoided, which may be described as therapy optimization.

The plot 340 is based on patient-specific characterization data. In other embodiments, a best-match patient CV model or classification-based CV model may be used.

A clinician or the therapy modeling system 200 (FIG. 4) may determine to test a therapy to elevate the heart rate above normal while avoiding over-taxing the heart (see test 270 and test 272 of FIG. 11). Patient characterization data, such as echocardiogram data and hemodynamic measurement data, may be used to configure the CV model.

The output data of the CV model may provide a simulated cardiac stroke work efficiency (normalized to baseline) versus heartrate (per minute) over a range of pacing rates from about 70 to about 150 HBPM.

The plot 340 shows two different sets of responses from CV models that were configured using two different sets of patient characterization data. The first data set 342 (illustrated with white diamonds) shows a maximum efficiency at about 100 HBPM. The second data set 344 (illustrated with black diamonds) shows a maximum efficiency around 125 HBPM. Depending on which data set 342, 344 corresponds with a particular patient's characterization data, the therapy modeling system 200 may determine one or more therapy parameters (for example, for an IMD) to provide HR pacing at the corresponding maximum efficiency. A visualization of the plot 340 may also be provided to the clinician.

In some embodiments, determining one or more therapy parameters may include determining a plurality of cardiac stroke work efficiencies each corresponding to a different pacing heart rate from a plurality of pacing heart rates using the CV model. The one or more therapy parameters may be determined to provide HFpEF therapy using a pacing heart rate corresponding to a maximum cardiac stroke work efficiency of the plurality of cardiac stroke work efficiencies.

Figure 15:
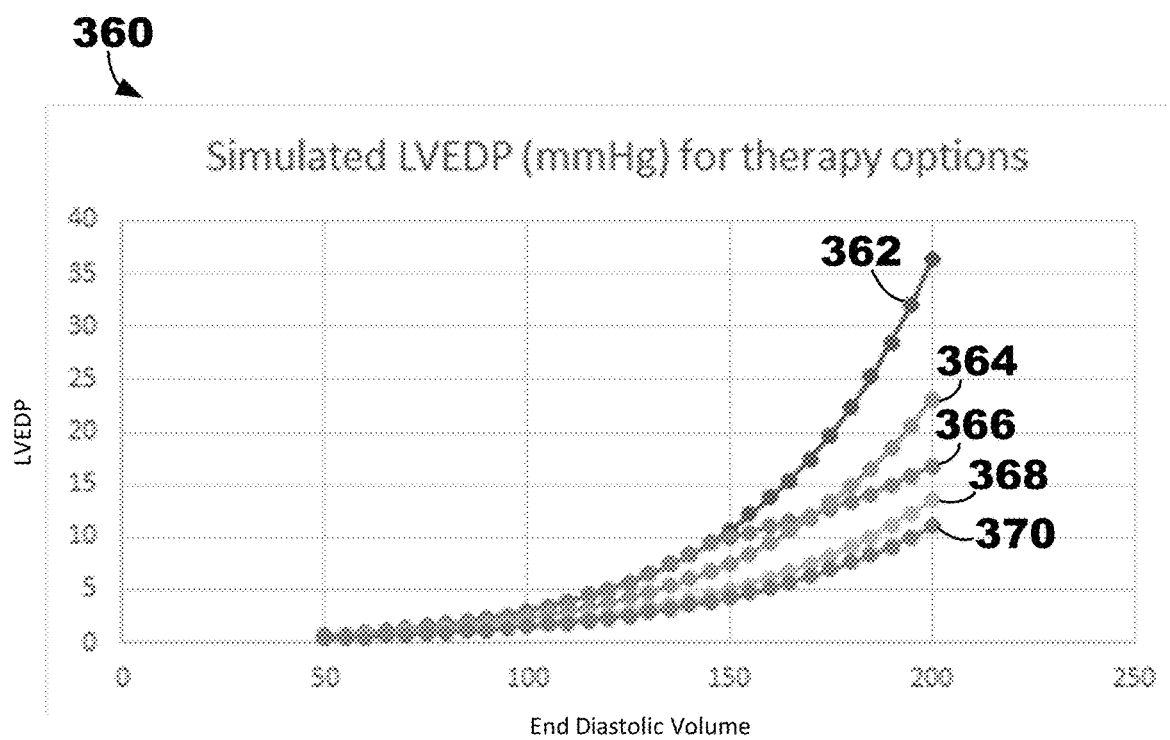
FIG. 15 is a diagram that illustrates one example of a plot of output data from a CV model for therapy selection usable with the therapy modeling system of FIG. 4.

FIG. 15 is a diagram that illustrates one example of a plot 360 of output data from a CV model, for example, as part of configuring the CV model 226 (FIG. 9) and determining one or more therapy parameters 228 (FIG. 9). In particular, the plot 360 may be used to predict a patient response to candidate therapies and to evaluate whether certain therapies should be avoided, which may be described as therapy selection.

A clinician or the therapy modeling system 200 (FIG. 4) may determine to test non-pacing interventions as possible candidate therapies. In particular, the interventions may be evaluated for ability to lower cardiac filling pressure (such as a left-ventricular end-diastolic pressure, or LVEDP).

Patient characterization data, such as imaging data (MRI or CT scan of the thorax) and hemodynamic measurement data (LV pressure), may be used to configure the CV model. The CV model may include the heart and circulatory system including the pericardium. The CV model may be a finite-element model.

The output data of the CV model may provide a simulated LVEDP (mmHg) versus end diastolic volume (mm) over a range of end diastolic volumes, such as 50 to 200 mm.

The plot 360 shows five different sets of responses from CV models that were configured to simulate different types of therapies. In particular, the plot 360 shows LVEDP values based on different CV models configured to represent a baseline LVEDP (no intervention) 362, a pericardial resection intervention 364, an interatrial shunting intervention 366, a trabecular cutting intervention 368, and a target LVEDP 370.

The plot 360 may be used to select the therapy or intervention that is closest to the target LVEDP 370. On example heuristic for selection is the smallest total sum of differences between a particular therapy and the target LVEDP 370. In the illustrated embodiment, the trabecular cutting intervention 368 may be recommended over the other interventions. The therapy modeling system 200 may determine the appropriate intervention as a therapy parameter and may communicate the therapy parameter to the clinician (for example, using the clinician interface system 130 of FIG. 4). A visualization of the plot 360 may also be provided to the clinician.

In some embodiments, testing non-pacing therapies includes using the CV model to provide output data including left ventricular end diastolic pressure (LVEDP) for various end diastolic volumes. In some embodiments, testing non-pacing therapy includes comparing non-pacing therapies to a target patient function, such as a target LVEDP versus end diastolic volume.

Figure 16:
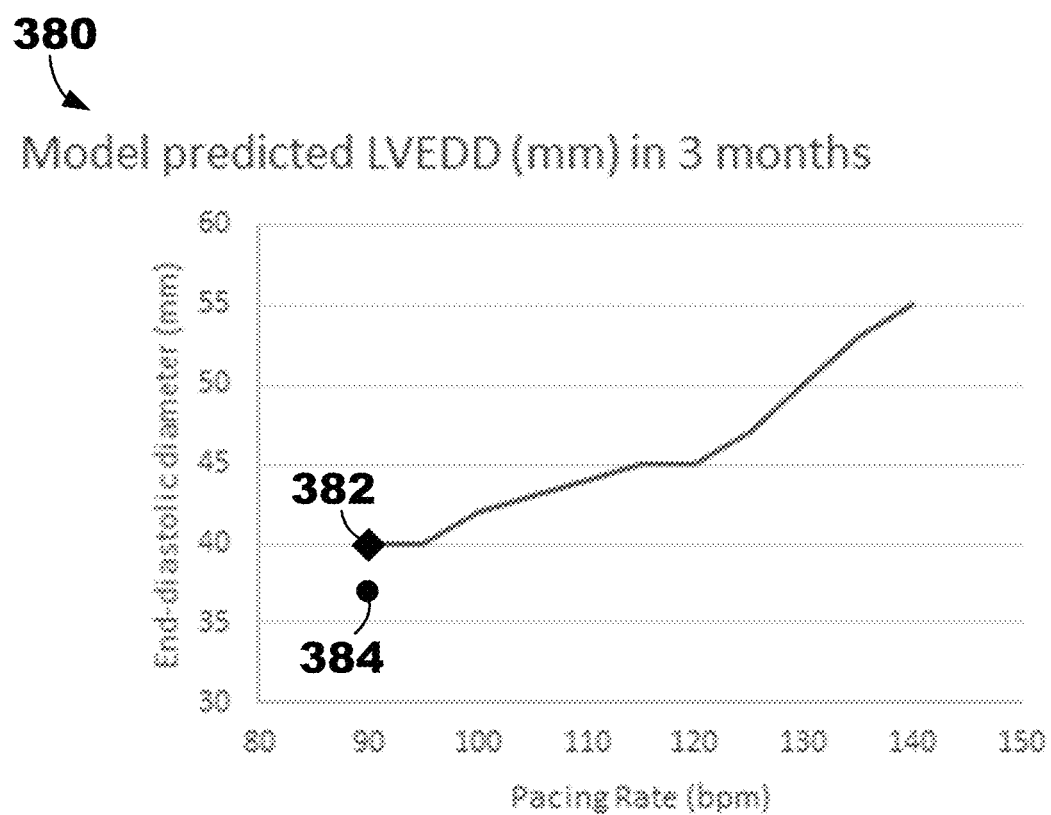
FIG. 16 is a diagram that illustrates one example of a plot of output data from a CV model for therapy titration usable with the therapy modeling system of FIG. 4.

FIG. 16 is a diagram that illustrates one example of a plot 380 of output data from a CV model, example, as part of configuring the CV model 226 (FIG. 9) and determining one or more therapy parameters 228 (FIG. 9). In particular, the plot 380 may be used to predict a patient response to a therapy over time and to configure the therapy based on the prediction, which may be described as therapy titration.

A clinician or the therapy modeling system 200 (FIG. 4) may determine to test the patient response to a particular therapy over time. In particular, the CV model may be used to update or guide the application of the therapy based on the predicted patient response. The output data of the CV model may be used to update the CV model based on patient response to facilitate targeting of a changing new optimal therapy or to determine whether certain therapies should be avoided. In some embodiments, testing the patient response to therapy over time may be used where rapid HR pacing is used for periods of time to increase the volume of the heart.

Patient characterization data, such as echocardiogram data and hemodynamic measurement data may be used to configure the CV model. The CV model may include at least the circulatory system.

The output data of the CV model may provide a simulated left ventricular end diastolic diameter (LVEDD) (mm) versus pacing rate (HBPM) over a range of pacing rates, such as 90 to 140. In particular, the output data of the CV model may provide a predicted LVEDD after a period of time after administering the therapy. In the illustrated embodiment, the plot 380 represents the predicted LVEDD 382 over various pacing rates after 3 months of administering the therapy.

The CV model may be used to sweep the different rate and durations to simulate the potential patient response. The therapy modeling system 200 may determine or adjust the target intervention heart rate based on the patient response indicated by the CV model. In the illustrated embodiment, the therapy modeling system 200 may select a pacing rate of 125 HBPM so that 47 mm LVEDD will occur around next follow-up visit in the clinic at 3 months.

In some embodiments, the therapy modeling system 200 may updating the CV model based on patient response data after administering HFpEF therapy and may update the HFpEF therapy based on the updated CV model. In some cases, the CV model may be updated at the next clinic visit. For example, the therapy administration may start using a nominal or patient classification-based pacing rate based on a starting LVEDD 384. In another example, the therapy administration may start using the optimized pacing rate determined using the CV model. At the 3 month visit, the CV model may be updated after updating patient characterization data. The target LVEDD may be reevaluated (for example, changed from 47 mm), and the pacing rate may be updated accordingly using the updated CV model to achieve the new target LVEDD.

In some embodiments, determining one or more therapy parameters may include determining a plurality of predicted patient characterization values each corresponding to a different therapy parameter value of a plurality of therapy parameter values using the CV model. Each predicted patient characterization value may indicate a predicted patient characterization value after administering HFpEF therapy using the corresponding therapy parameter value over a selected period of time based on the CV model. A target therapy parameter value may be determined from the different therapy parameter values based on a target patient characterization parameter and the plurality of predicted patient characterization values. The one or more therapy parameters may be determined to provide HFpEF therapy using the target therapy parameter value.

Figure 17:
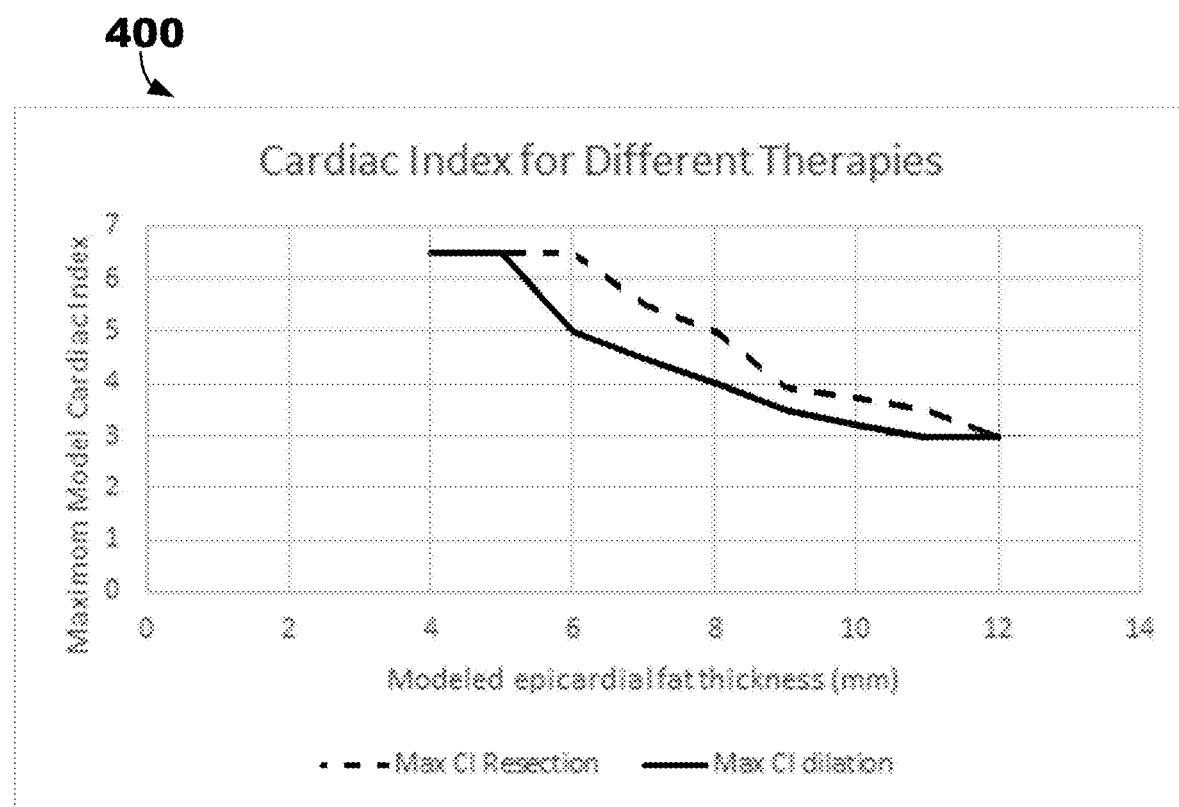
FIG. 17 is a diagram that illustrates one example of a plot of output data from a CV model for therapy sequencing usable with the therapy modeling system of FIG. 4.

FIG. 17 is a diagram that illustrates one example of a plot 400 of output data from a CV model, example, as part of configuring the CV model 226 (FIG. 9) and determining one or more therapy parameters 228 (FIG. 9). In particular, the plot 400 may be used to identify or determine an enabling therapy for another therapy, which may be described as therapy sequencing.

A clinician or the therapy modeling system 200 (FIG. 4) may determine to guide two or more therapies, which may include an enabling therapy. In one example, the clinician or therapy modeling system 200 may determine whether a particular therapy is effective. In response to the particular therapy being not effective, the therapy modeling system 200 may determine whether an enabling therapy may be used to initiate a patient response that may enable the particular patient therapy using the CV model. The enabling therapy may be administered, and the patient characterization data may be updated, until the patient characterization data indicates that the particular therapy may be successful.

In some embodiments, the therapy modeling system 200 may identify a factor that may keep a particular therapy from working until the factor is addressed and may identify one or more therapy parameters for an enabling therapy. In one example, an obese patient may have fat deposits on the heart. The CV model may be used to determine which patient parameters can be changed to allow dilation therapy, or HFpEF therapy with increased HR pacing, to work.

Patient characterization data, such as imaging data (MRI or CT scan), may be used to configure the CV model. The CV model may include the heart and circulatory system including the pericardium. The CV model may be a finite-element model.

In some embodiments, the output data of the CV model provide cardiac output (CO) or cardiac index (CI) versus modeled epicardial fat thickness (mm) over a range of thicknesses, such as 4 to 12 mm. The epicardial fat deposit size in the CV model may be varied to determine an intervention's effectiveness under different epicardial fat scenarios.

The plot 400 shows two different sets of responses from CV models that were configured to simulate different types of therapies. In particular, the plot 400 shows CI values based on different CV models configured to represent HFpEF pacing therapy 402 and pericardial resection therapy 404.

In the illustrated embodiment, none of the particular therapies 402, 404 are effective in effectively increasing CI above 6 until epicardial fat is reduced from 12 to about 5 to 6 mm. The therapy modeling system 200 may determine to provide an enabling therapy, such as determining to administer an SGLT2 inhibitor drug. The enabling therapy may be administered by the clinician or a therapy delivery system. The patient characterization data may be monitored or updated until epicardial fat reduction is obtained. The CV model may be updated based on the updated patient characterization data to help determine when conditions are met to allow one or both of the particular therapies 402, 404 to be effective in increasing CI (for example, above 6). Once the conditions are met for the patient, administration of enabling therapy may be stopped and one or the particular therapies 402, 404 may be selected, for example, using therapy selection techniques described herein.

In some embodiments, determining one or more therapy parameters may include determining one or more enabling therapies using the CV model. Modified patient characterization data may be provided to the CV model (such as modified epicardial fat thicknesses). Whether the modified patient characterization data enables HFpEF therapy is determined (such as epicardial fat thickness below 5 or 6 mm). One or more enabling therapies may be selected based on the modified patient characterization data in response to determining that the modified patient characterization data enables HFpEF therapy.

Illustrative Embodiments

While the present disclosure is not so limited, an appreciation of various aspects of the disclosure will be gained through a discussion of illustrative embodiments provided below. Various modifications of the illustrative embodiments, as well as additional embodiments of the disclosure, will become apparent herein.

A1. A method comprising:
  determining that a patient has heart failure with preserved ejection fraction (HFpEF);
  configuring a cardiovascular (CV) model using patient characterization data;
  determining one or more therapy parameters using output data of the CV model; and
  administering HFpEF therapy based on the one or more therapy parameters.

A2. The method according to Embodiment A1, wherein determining one or more therapy parameters comprises testing pacing therapy by an implantable medical device (IMD) using the CV model.

A3. The method according to Embodiment A2, wherein administering HFpEF therapy comprises configuring the IMD and administering pacing therapy using the IMD, wherein the one or more therapy parameters includes one or more of the following: a type of pacing therapy, a pacing rate, a sensing or pacing location, a pacing duration, a pacing duty cycle, or a pacing frequency.

A4. The method according to any preceding A Embodiment, further comprising determining patient characterization data to configure the CV model based on one or more of the following: clinician input data, electrode apparatus data, echocardiogram data, imaging data, patient history data, hemodynamic measurement data, or implantable medical device (IMD) data.

A5. The method according to any preceding A Embodiment, wherein determining one or more therapy parameters using output data of the CV model comprises determining one or more candidate therapies using the CV model.

A6. The method according to any preceding A Embodiment, wherein configuring the CV model using patient characterization data is based on the patient characterization data indicating whether the patient has atrial fibrillation (AF).

A7. The method according to Embodiment A6, wherein configuring the CV model using patient characterization data is further based on the patient characterization data indicating whether the patient has a left bundle branch block in response to the patient characterization data indicating that the patient has AF.

A8. The method according to Embodiment A6, wherein determining one or more therapy parameters using output data of the CV model comprises testing a plurality of different pacing therapies to identify acceptable atrioventricular delays using the CV model in response to the patient characterization data indicating that the patient does not have AF.

A9. The method according to any preceding A Embodiment, wherein configuring the CV model using patient characterization data is based on the patient characterization data indicating whether the patient has concentric hypertrophy or concentric remodeling.

A10. The method according to Embodiment A9, wherein determining one or more therapy parameters using output data of the CV model comprises testing a first elevated heart rate pacing to relieve symptoms using the CV model in response to the patient characterization data not indicating atrial fibrillation and not indicating concentric hypertrophy or concentric remodeling.

A11. The method according to Embodiment A9, wherein determining one or more therapy parameters using output data of the CV model comprises testing a second elevated heart rate pacing to remodel using the CV model in response to the patient characterization data indicating concentric hypertrophy or concentric remodeling.

A12. The method according to any preceding A Embodiment, wherein configuring the CV model using patient characterization data is based on the patient characterization data indicating whether the patient has an intra-atrial conduction delay.

A13. The method according to Embodiment A12, wherein determining one or more therapy parameters using output data of the CV model comprises testing atrial resynchronization pacing therapy using the CV model in response to the patient characterization data indicating that the patient has an intra-atrial conduction delay.

A14. The method according to Embodiment A13, wherein testing atrial resynchronization pacing therapy using the CV model comprises one or more of the following: testing Bachmann's bundle pacing, testing biatrial pacing, or testing left atrial fusion pacing.

A15. The method according to Embodiment A12, wherein determining one or more therapy parameters using output data of the CV model comprises determining the one or more therapy parameters to provide no atrial resynchronization pacing therapy in response to the patient characterization data indicating that the patient has no intra-atrial conduction delay.

A16. The method according to any preceding A Embodiment, wherein determining one or more therapy parameters using output data of the CV model comprises testing ventricular resynchronization pacing therapy using the CV model in response to the patient characterization data indicating that the patient has a left bundle branch block (LBBB).

A17. The method according to Embodiment A16, wherein testing ventricular resynchronization pacing therapy using the CV model comprises one or more of the following: testing left bundle branch (LBB) pacing, testing His bundle pacing, testing left ventricular pacing, or testing bi-ventricular pacing.

A18. The method according to Embodiment A16, wherein determining one or more candidate therapies using the CV model comprises determining the one or more therapy parameters to provide no cardiac resynchronization pacing therapy in response to the patient characterization data indicating that the patient does not have an LBBB.

A19. The method according to any preceding A Embodiment, wherein determining one or more therapy parameters using output data of the CV model comprises:
  determining a plurality of cardiac dyssynchrony measure values using the CV model each measure value corresponding to a different test ventricular resynchronization therapy;
  determining whether any of the cardiac dyssynchrony measure values indicate a reduction from a baseline patient cardiac dyssynchrony measure value greater than or equal to a reduction threshold;
  in response to determining that none of the cardiac dyssynchrony measure values indicate a reduction of greater than or equal to the reduction threshold, determining the one or more therapy parameters to provide no ventricular resynchronization pacing therapy;
  in response to determining that at least one of the cardiac dyssynchrony measure values indicates a reduction greater than or equal to the reduction threshold,
  determining a largest reduction cardiac dyssynchrony measure value corresponding to a largest reduction in cardiac dyssynchrony from the baseline patient cardiac dyssynchrony measure value, and
  determining whether the largest reduction cardiac dyssynchrony measure value is greater than the other cardiac dyssynchrony measure values by at least a comparative threshold; and
  in response to determining that the largest reduction cardiac dyssynchrony measure value is greater than the other cardiac dyssynchrony measure values by at least the comparative threshold, determining the one or more therapy parameters to provide ventricular resynchronization pacing therapy corresponding to the largest reduction cardiac dyssynchrony measure value.

A20. The method according to Embodiment A19, wherein determining one or more therapy parameters using output data of the CV model further comprises:
  in response to determining that the largest reduction cardiac dyssynchrony measure value is not greater than the other cardiac dyssynchrony measure values by at least the comparative threshold, discarding any cardiac dyssynchrony measure values not within range of the largest reduction cardiac dyssynchrony measure value by the comparative threshold;
  determining which of the cardiac dyssynchrony measure values correspond to a maximum LV stroke work using the CV model; and
  determining the one or more therapy parameters to provide ventricular resynchronization pacing therapy based on the cardiac dyssynchrony measure value corresponding to the maximum LV stroke work.

A21. The method according to any preceding A Embodiment, wherein determining one or more therapy parameters using output data of the CV model comprises:
  determining a plurality of cardiac stroke work efficiencies each corresponding to a different pacing heart rate from a plurality of pacing heart rates using the CV model; and
  determining the one or more therapy parameters to provide HFpEF therapy using a pacing heart rate corresponding to a maximum cardiac stroke work efficiency of the plurality of cardiac stroke work efficiencies.

A22. The method according to any preceding A Embodiment, wherein determining one or more therapy parameters using output data of the CV model comprises:
  determining a plurality of predicted patient characterization values each corresponding to a different therapy parameter value of a plurality of therapy parameter values using the CV model, wherein each predicted patient characterization value indicates a predicted patient characterization value after administering HFpEF therapy using the corresponding therapy parameter value over a selected period of time based on the CV model;
  determining a target therapy parameter value from the different therapy parameter values based on a target patient characterization parameter and the plurality of predicted patient characterization values; and
  determining the one or more therapy parameters to provide HFpEF therapy using the target therapy parameter value.

A23. The method according to any preceding A Embodiment, wherein determining one or more therapy parameters using output data of the CV model comprises determining one or more enabling therapies using the CV model.

A24. The method according to Embodiment A23, wherein determining one or more enabling therapies using the CV model comprises:
  providing modified patient characterization data to the CV model;
  determining whether the modified patient characterization data enables HFpEF therapy; and
  selecting one or more enabling therapies based on the modified patient characterization data in response to determining that the modified patient characterization data enables HFpEF therapy.

A25. The method according to any preceding A Embodiment, further comprising updating the CV model based on patient response data after administering HFpEF therapy and updating HFpEF therapy based on the updated CV model.

A26. The method according to Embodiment A25, further comprising determining the patient response data based on updated patient characterization data measured using an implantable medical device (IMD) and providing the updated patient characterization data over the internet to a remote therapy management system, wherein the CV model is executed by processing circuitry of the remote therapy management system.

A27. The method according to Embodiment A25 or A26, wherein updating the CV model based on patient response data after administering HFpEF therapy comprises updating the CV model based on a predicted patient characterization value and a measured patient characterization value after administering HFpEF therapy.

A28. The method according to any preceding Embodiment, wherein administering HFpEF therapy comprises administering a non-pacing therapy by a clinician.

A29. The method according to any preceding A Embodiment, wherein determining one or more therapy parameters comprises testing non-pacing therapy by a clinician using the CV model.

A30. The method according to any preceding A Embodiment, wherein testing non-pacing therapy comprises testing one or more of the following non-pacing therapies: interatrial shunting, pericardial resection, or trabecular cutting.

B1. A non-transient computer-readable storage medium comprising computing instructions stored thereon that, when executed by processing circuitry, cause the processing circuitry to perform operations as defined in any A Embodiment.

C1. A controller comprising:
an input interface configured to receive patient characterization data;
an output interface configured to provide therapy parameter data; and
processing circuitry operably coupled to the input interface and the output interface, the processing circuitry configured to:
receive the patient characterization data in response to determining that a patient has heart failure with preserved ejection fraction (HFpEF);
configure a cardiovascular (CV) model using the patient characterization data;
determine one or more therapy parameters using output data of the CV model; and
provide therapy parameter data comprising the one or more therapy parameters to the output interface.

C2. The controller according to Embodiment C1, wherein the processing circuitry is further configured to perform the method according to any A Embodiment.

D1. A system comprising:
one or more patient characterization devices to provide patient characterization data;
an implantable medical device (IMD) configured to provide heart failure with preserved ejection fraction (HFpEF) pacing therapy; and
processing circuitry operably coupled to the one or more patient characterization devices and the implantable medical device, the processing circuitry configured to:
receive the patient characterization data in response to determining that a patient has HFpEF;
configure a cardiovascular (CV) model using the patient characterization data;
determine one or more therapy parameters using output data of the CV model; and
configure the IMD to provide HFpEF pacing therapy based on the one or more therapy parameters.

D2. The system according to Embodiment D1, wherein the processing circuitry is further configured to perform the method according to any A Embodiment.

Thus, various embodiments of model-based therapy parameters for heart failure are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (for example, all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (for example, RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The singular forms "a," "an," and "the" encompass embodiments having plural referents unless its context clearly dictates otherwise.

What is claimed is:

1. A method comprising:
determining that a patient has heart failure with preserved ejection fraction (HFpEF);
configuring a cardiovascular (CV) model using patient characterization data;
determining one or more HFpEF therapy parameters using output data of the CV model; and
administering HFpEF therapy based on the one or more HFpEF therapy parameters.

2. The method according to claim 1, wherein determining one or more HFpEF therapy parameters comprises testing pacing therapy by an implantable medical device (IMD) using the CV model.

3. The method according to claim 2, wherein administering HFpEF therapy comprises configuring the IMD and administering pacing therapy using the IMD, wherein the one or more HFpEF therapy parameters includes one or more of the following: a type of pacing therapy, a pacing rate, a sensing or pacing location, a pacing duration, a pacing duty cycle, or a pacing frequency.

4. The method according to claim 1, further comprising determining the patient characterization data to configure the CV model based on one or more of the following: clinician input data, electrode apparatus data, echocardiogram data, imaging data, patient history data, hemodynamic measurement data, or implantable medical device (IMD) data.

5. The method according to claim 1, wherein determining one or more HFpEF therapy parameters using output data of the CV model comprises determining one or more candidate therapies using the CV model.

6. The method according to claim 5, wherein determining one or more candidate therapies using the CV model comprises determining the one or more HFpEF therapy parameters to provide no cardiac resynchronization pacing therapy in response to the patient characterization data indicating that the patient does not have an LBBB.

7. The method according to claim 1, wherein configuring the CV model using patient characterization data is based on the patient characterization data indicating whether the patient has atrial fibrillation (AF).

8. The method according to claim 7, wherein configuring the CV model using patient characterization data is further based on the patient characterization data indicating whether the patient has a left bundle branch block in response to the patient characterization data indicating that the patient has AF.

9. The method according to claim 7, wherein determining one or more HFpEF therapy parameters using output data of the CV model comprises testing a plurality of different pacing therapies to identify acceptable atrioventricular delays using the CV model in response to the patient characterization data indicating that the patient does not have AF.

10. The method according to claim 1, wherein configuring the CV model using patient characterization data is based on the patient characterization data indicating whether the patient has concentric hypertrophy or concentric remodeling.

11. The method according to claim 10, wherein configuring the CV model using patient characterization data is further based on the patient characterization data indicating whether the patient has atrial fibrillation (AF), wherein determining one or more HFpEF therapy parameters using output data of the CV model comprises testing a first elevated heart rate pacing to relieve symptoms using the CV model in response to the patient characterization data not indicating atrial fibrillation and not indicating concentric hypertrophy or concentric remodeling.

12. The method according to claim 10, wherein determining one or more HFpEF therapy parameters using output data of the CV model comprises testing a second elevated heart rate pacing to remodel using the CV model in response to the patient characterization data indicating concentric hypertrophy or concentric remodeling.

13. The method according to claim 1, wherein configuring the CV model using patient characterization data is based on the patient characterization data indicating whether the patient has an intra-atrial conduction delay.

14. The method according to claim 13, wherein determining one or more HFpEF therapy parameters using output data of the CV model comprises testing atrial resynchronization pacing therapy using the CV model in response to the patient characterization data indicating that the patient has an intra-atrial conduction delay.

15. The method according to claim 14, wherein testing atrial resynchronization pacing therapy using the CV model comprises one or more of the following: testing Bachmann's bundle pacing, testing biatrial pacing, or testing left atrial fusion pacing.

16. The method according to claim 13, wherein determining one or more HFpEF therapy parameters using output data of the CV model comprises determining the one or more HFpEF therapy parameters to provide no atrial resynchronization pacing therapy in response to the patient characterization data indicating that the patient has no intra-atrial conduction delay.

17. The method according to claim 1, wherein determining one or more HFpEF therapy parameters using output data of the CV model comprises testing ventricular resynchronization pacing therapy using the CV model in response to the patient characterization data indicating that the patient has a left bundle branch block (LBBB).

18. The method according to claim 17, wherein testing ventricular resynchronization pacing therapy using the CV model comprises one or more of the following: testing left bundle branch (LBB) pacing, testing His bundle pacing, testing left ventricular pacing, or testing bi-ventricular pacing.

19. The method according to claim 1, wherein determining one or more HFpEF therapy parameters using output data of the CV model comprises:
   determining a plurality of cardiac dyssynchrony measure values using the CV model, each cardiac dyssynchrony measure value corresponding to a different test ventricular resynchronization therapy;
   determining whether any of the cardiac dyssynchrony measure values indicate a reduction from a baseline patient cardiac dyssynchrony measure value greater than or equal to a reduction threshold;
   in response to determining that none of the cardiac dyssynchrony measure values indicate a reduction of greater than or equal to the reduction threshold, determining the one or more HFpEF therapy parameters to provide no ventricular resynchronization pacing therapy;
   in response to determining that at least one of the cardiac dyssynchrony measure values indicates a reduction greater than or equal to the reduction threshold,
      determining a largest reduction cardiac dyssynchrony measure value corresponding to a largest reduction in cardiac dyssynchrony from the baseline patient cardiac dyssynchrony measure value, and
      determining whether the largest reduction cardiac dyssynchrony measure value is greater than the other cardiac dyssynchrony measure values by at least a comparative threshold; and
   in response to determining that the largest reduction cardiac dyssynchrony measure value is greater than the other cardiac dyssynchrony measure values by at least the comparative threshold, determining the one or more HFpEF therapy parameters to provide ventricular resynchronization pacing therapy corresponding to the largest reduction cardiac dyssynchrony measure value.

20. The method according to claim 19, wherein determining one or more HFpEF therapy parameters using output data of the CV model further comprises:
   in response to determining that the largest reduction cardiac dyssynchrony measure value is not greater than the other cardiac dyssynchrony measure values by at least the comparative threshold, discarding any cardiac dyssynchrony measure values not within range of the largest reduction cardiac dyssynchrony measure value by the comparative threshold;
   determining which of the cardiac dyssynchrony measure values correspond to a maximum LV stroke work using the CV model; and
   determining the one or more therapy parameters to provide ventricular resynchronization pacing therapy based on the cardiac dyssynchrony measure value corresponding to the maximum LV stroke work.

21. The method according to claim 1, wherein determining one or more HFpEF therapy parameters using output data of the CV model comprises:
   determining a plurality of cardiac stroke work efficiencies, each cardiac stroke work efficiency corresponding to a different pacing heart rate from a plurality of pacing heart rates using the CV model; and
   determining the one or more HFpEF therapy parameters to provide HFpEF therapy using a pacing heart rate corresponding to a maximum cardiac stroke work efficiency of the plurality of cardiac stroke work efficiencies.

22. The method according to claim 1, wherein determining one or more HFpEF therapy parameters using output data of the CV model comprises:
   determining a plurality of predicted patient characterization values, each predicted patient characterization value corresponding to a different HFpEF therapy parameter value of a HFpEF plurality of therapy parameter values using the CV model, wherein each predicted patient characterization value indicates a predicted patient characterization value after administering HFpEF therapy using the corresponding HFpEF therapy parameter value over a selected period of time based on the CV model;
   determining a target HFpEF therapy parameter value from the different HFpEF therapy parameter values based on a target patient characterization parameter and the plurality of predicted patient characterization values; and
   determining the one or more HFpEF therapy parameters to provide HFpEF therapy using the target HFpEF therapy parameter value.

23. The method according to claim 1, wherein determining one or more HFpEF therapy parameters using output data of the CV model comprises determining one or more enabling therapies using the CV model.

24. The method according to claim 23, wherein determining one or more enabling therapies using the CV model comprises:
   providing modified patient characterization data to the CV model;
   determining whether the modified patient characterization data enables HFpEF therapy; and
   selecting one or more enabling therapies based on the modified patient characterization data in response to determining that the modified patient characterization data enables HFpEF therapy.

25. The method according to claim 1, further comprising updating the CV model based on patient response data after administering HFpEF therapy and updating HFpEF therapy based on the updated CV model.

26. The method according to claim 25, further comprising determining the patient response data based on updated patient characterization data measured using an implantable medical device (IMD) and providing the updated patient characterization data over the internet to a remote therapy management system, wherein the CV model is executed by processing circuitry of the remote therapy management system.

27. The method according to claim 25, wherein updating the CV model based on patient response data after administering HFpEF therapy comprises updating the CV model based on a predicted patient characterization value and a measured patient characterization value after administering HFpEF therapy.

28. The method according to claim 1, wherein administering HFpEF therapy comprises administering a non-pacing therapy by a clinician.

29. The method according to claim 1, wherein determining one or more HFpEF therapy parameters comprises testing non-pacing therapy by a clinician using the CV model.

30. The method according to claim 29, wherein testing non-pacing therapy comprises testing one or more of the following non-pacing therapies: interatrial shunting, pericardial resection, or trabecular cutting.

31. A non-transient computer-readable storage medium comprising computing instructions stored thereon that, when executed by processing circuitry, cause the processing circuitry to perform operations as defined in claim 1.

32. A controller comprising:
   an input interface configured to receive patient characterization data;
   an output interface configured to provide therapy parameter data; and
   processing circuitry operably coupled to the input interface and the output interface, the processing circuitry configured to:
     receive patient characterization data in response to determining that a patient has heart failure with preserved ejection fraction (HFpEF);
     configure a cardiovascular (CV) model using the patient characterization data;
     determine one or more HFpEF therapy parameters using output data of the CV model; and
     provide therapy parameter data comprising the one or more HFpEF therapy parameters to the output interface.

33. The controller according to claim 32, wherein the processing circuitry is further configured to administer HFpEF therapy based on the one or more HFpEF therapy parameters.

34. A system comprising:
   one or more patient characterization devices to provide patient characterization data;
   an implantable medical device (IMD) configured to provide heart failure with preserved ejection fraction (HFpEF) pacing therapy; and
   processing circuitry operably coupled to the one or more patient characterization devices and the implantable medical device, the processing circuitry configured to:
     receive patient characterization data in response to determining that a patient has HFpEF;
     configure a cardiovascular (CV) model using the patient characterization data;
     determine one or more HFpEF therapy parameters using output data of the CV model; and
     configure the IMD to provide HFpEF pacing therapy based on the one or more HFpEF therapy parameters.

35. The system according to claim 34, wherein the processing circuitry is further configured to administer HFpEF therapy based on the one or more HFpEF therapy parameters.

* * * * *